US009446114B2

(12) United States Patent
Broderick et al.

(10) Patent No.: US 9,446,114 B2
(45) Date of Patent: Sep. 20, 2016

(54) CROSS-PROTECTIVE ARENAVIRUS VACCINES AND THEIR METHOD OF USE

(75) Inventors: Kate Broderick, San Diego, CA (US); Niranjan Sardesai, Blue Bell, PA (US); Kathleen Cashman, Purcellville, VA (US); Connie Schmaljohn, Middletown, MD (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 0 days.

(21) Appl. No.: 14/232,110

(22) PCT Filed: Jul. 11, 2012

(86) PCT No.: PCT/US2012/046318
§ 371 (c)(1),
(2), (4) Date: Apr. 18, 2014

(87) PCT Pub. No.: WO2013/055418
PCT Pub. Date: Apr. 18, 2013

(65) Prior Publication Data

US 2014/0249467 A1 Sep. 4, 2014

Related U.S. Application Data

(60) Provisional application No. 61/507,062, filed on Jul. 12, 2011, provisional application No. 61/506,579, filed on Jul. 11, 2011.

(51) Int. Cl.
*A61K 39/12* (2006.01)
*A61N 1/32* (2006.01)
*A61K 39/00* (2006.01)

(52) U.S. Cl.
CPC ............... *A61K 39/12* (2013.01); *A61N 1/327* (2013.01); *A61K 2039/53* (2013.01); *A61K 2039/54* (2013.01); *C12N 2760/10022* (2013.01); *C12N 2760/10034* (2013.01)

(58) Field of Classification Search
None
See application file for complete search history.

(56) References Cited

FOREIGN PATENT DOCUMENTS

| | | | |
|---|---|---|---|
| WO | WO2007/093449 A2 * | 8/2007 | |
| WO | 2008/124176 | 10/2008 | |
| WO | 2011/034953 | 3/2011 | |

OTHER PUBLICATIONS

Rodriguez-Carreno et al. Evaluating the immunogenicity and protective efficacy of a DNA vaccine encoding Lassa virus nucleoprotein. Virology. Apr. 25, 2005;335(1):87-98.*
Fisher-Hoch et al. Effective vaccine for Lassa fever. J. of Virol. 2000, 74: 6777-6783.*
Tenbusch et al. Codon-optimization of the hemagglutinin gene from the novel swine origin H1N1 influenza virus has differential effects on CD4(+) T-cell responses and immune effector mechanisms following DNA electroporation in mice. Vaccine. Apr. 26, 2010;28(19):3273-7. Epub Mar. 4, 2010.*
Roos et al. Skin electroporation: effects on transgene expression, DNA persistence and local tissue environment. PLoS One. Sep. 30, 2009;4(9):e7226.*
Ma et al. Coimmunization with RANTES plasmid polarized Th1 immune response against hepatitis B virus envelope via recruitment of dendritic cells. Antiviral Res. Nov. 2007;76(2):140-9. Epub Jul. 16, 2007.*
GenBank: AAT49004.1. glycoprotein precursor [Lassa virus]. Aug. 18, 2004.*
Shedlock, et al. A highly optimized DNA vaccine confers complete protective immunity against high-dose lethal lymphocytic choriomeningitis virus challenge. Vaccine Epub Jan. 14, 2011, 29(39):6755-62.
Kotturi, et al. A multivalent and cross-protective vaccine strategy against arenaviruses associated with human disease. PLoS Pathog. 2009, 5(12):e1000695.
Botten, et al. A multivalent vaccination strategy for the prevention of Old World arenavirus infection in humans. J Virol. 2010, 84(19):9947-9956.
NCBI Reference Sequence: NP_694870.1; glycoprotein [Lassa virus], Dec. 8, 2008.
Ma, et al. Coimmunization with RANTES plasmid polarized Th1 immune response against hepatitis B virus envelope via recruitment of dendritic cells. Antiviral Research 76 (Jun. 19, 2007) pp. 140-149.
Roos, et al. Skin Electroporation: Effects on Transgene Expression, DNA Persistence and Local Tissue Environment. PLoS ONE, Sep. 30, 2009; V4, Issue 9; e7226.
Geisbert, et al. Development of a New Vaccine for the Prevention of Lassa Fever. PLoS Medicine, Jun. 2005 V2, Issue 6, e183.
Cashman, et al. Enhanced Efficacy of a Codon-Optimized DNA Vaccine Encoding the Glycoprotein Precursor Gene of Lassa Virus . . . Vaccines, Jul. 18, 2013, pp. 262-277.

* cited by examiner

*Primary Examiner* — Nick Zou
(74) *Attorney, Agent, or Firm* — Thomas Kim

(57) ABSTRACT

The invention relates to DNA vaccines that target multiple arenavirus agents singly or simultaneously.

8 Claims, 12 Drawing Sheets

Figure 1

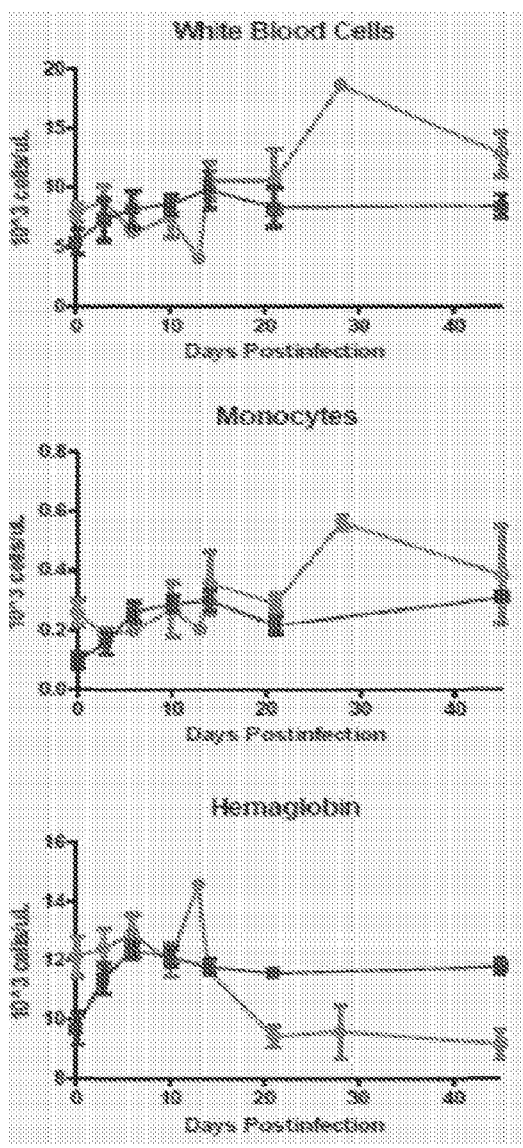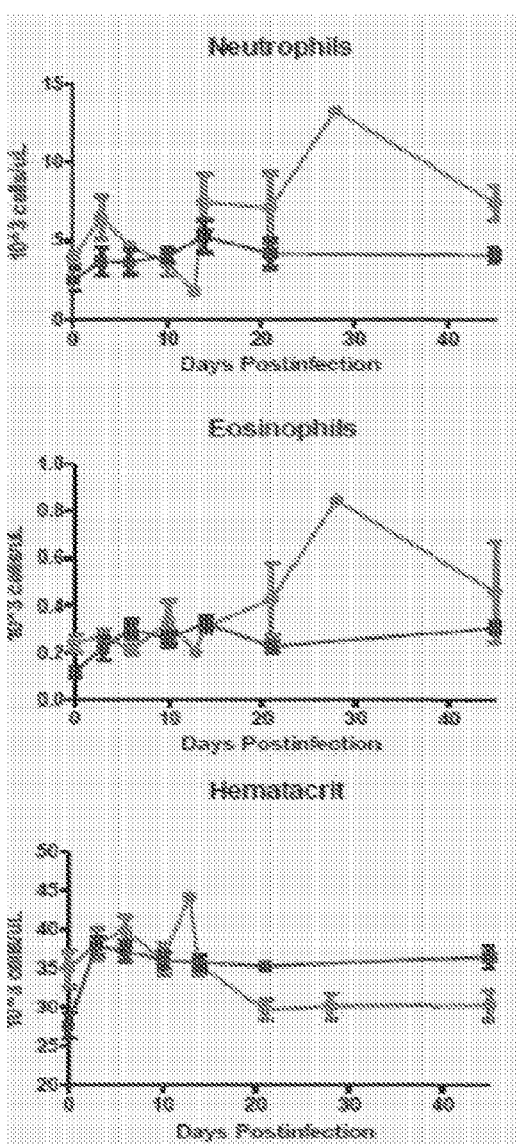

CROSS-PROTECTIVE ARENAVIRUS VACCINES AND THEIR METHOD OF USE

CROSS-REFERENCE TO RELATED APPLICATIONS

This application claims the benefit of U.S. Provisional Application Nos. 61/506,579, filed Jul. 11, 2011 and 61/507,062, filed Jul. 12, 2011, the content of which is incorporated herein by reference in its entirety.

FEDERALLY-SPONSORED RESEARCH AND DEVELOPMENT

Activities relating to the development of the subject matter of this invention were funded at least in part by U.S. Government, Army Contract No. W81XWH-12-0154, and thus the U.S. may have certain rights in the invention.

FIELD OF THE INVENTION

The present invention relates to DNA based vaccines effective in eliciting a protective immune response against arena viruses, and methods of making and using the same.

BACKGROUND OF THE INVENTION

Arenaviruses (AV) are rodent-borne viruses that cause an acute and often fatal hemorrhagic fever with associated malaise, severe edema, blood loss and a high mortality rate. Lassa virus (LASV) is an Old World arenavirus endemic to regions of West Africa. Imported cases of Lassa fever have been reported in the United States, Europe and Canada. It is estimated that between 300,000 and 500,000 cases of Lassa fever occur each year, with mortality rates of 15%-20% in hospitalized patients. New World arenaviruses, Junin (JUNV), Machupo (MACV), Guanarito, and Sabia viruses, are endemic to South America and are known to cause thousands of cases of severe hemorrhagic fever per year. Arena viruses are CDC Category A biological threat agents, and in the unfortunate event of an emerging disease outbreak or bioterror attack with these viruses there would be no FDA approved pre- or post-exposure therapeutic or vaccine available to the public. There has been reported studies that have identified HLA class I-restricted epitopes that can elicit an immune response in mice. See Botten, J., et al., J. Vir. 9947-9956 (October 2010).

For all the recent attention given to arenaviruses due to the outbreaks and the high degree of morbidity and mortality, there are very few treatments available. No licensed vaccine exists for AV prophylaxis and the only licensed drug for treatment of human AV infection is the anti-viral drug ribavirin. Ribavirin helps reduce morbidity and mortality associated with AV infection if taken early on exposure, but suffers from high toxicity and side effects. There is a clear unmet need to develop low cost and/or efficacious drugs for treatment and effective vaccines for prophylaxis in the AV endemic areas of the world as well as for combating exposure via a biodefense threat or through deployment of US military personnel in endemic parts of the world.

Furthermore, there also exists an unmet need for a multiagent arenavirus vaccine. As noted earlier there are no competitive effective prophylaxes or therapies available. To our knowledge the Junin live attenuated virus vaccine (Candid #1) approved for limited use under an investigational new drug (IND) status by the FDA is the only vaccine tested for arena virus infections. However, this vaccine was also subsequently shown in animal studies to not be able to cross-protect against other arenavirus strains.

Thus, there remains a need for a vaccine that provides an efficacious drug or effective vaccine for arenaviruses, and a vaccine that targets multiple arenavirus agents singly or simultaneously.

BRIEF DESCRIPTION OF THE DRAWINGS

FIGS. 1(A), 1(B), 1(C), and 1(D) display Serum viremia and morbidity scores for guinea pigs vaccinated with the non-optimized (comprising SEQ ID NO:3) versus optimized constructs (comprising SEQ ID NO:1).

FIGS. 1(B2) and 1(D2) display the data of FIGS. 1(B) and 1(D) but adds the serum viremia scores and morbidity scores, respectively, of non-invasive electroporation (NIVEP).

FIGS. 6(A), 6(B), and 6(C) display the selected blood chemistry values for *cynomolgus macaque* receiving the LASV-GPC (comprising SEQ ID NO:2) or mock (comprising SEQ ID NO:3) DNA vaccine.

DETAILED DESCRIPTION

Figure 2:
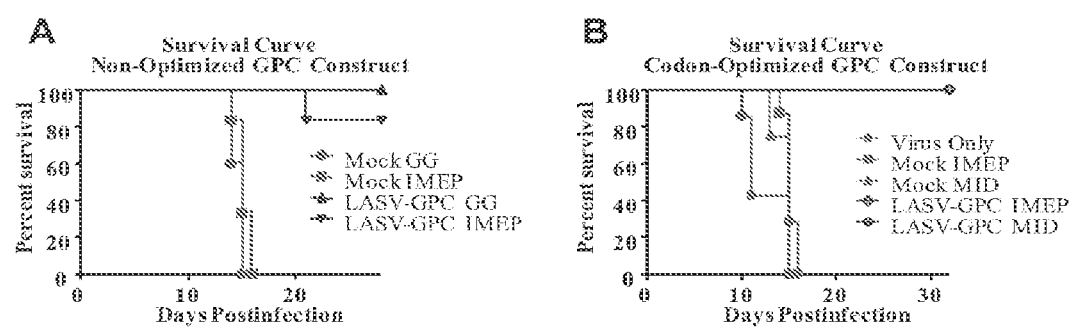
FIGS. 2(A) and 2(B) display survival curves for the non-optimized (comprising SEQ ID NO:3) and codon-optimized (comprising SEQ ID NO:1) LASV DNA Vaccine in guinea pigs.

An aspect of the invention provides for DNA vaccines that include a nucleotide coding sequence that encodes one or more immunogenic proteins capable of generating a protective immune response against an arenavirus in a subject in need thereof. The coding sequence encodes a glycoprotein precursor of an arenavirus, and are codon optimized for the subject of interest. In addition, the coding sequence can be an immunogenic fragment thereof that is at least 98% homologous to the glycoprotein precursor.

In some embodiments, the coding sequence consists essentially of glycoprotein precursor domain of LASV (LASV-GPC), glycoprotein precursor domain of LCMV (LCMV-GPC), glycoprotein precursor domain of MACV (MACV-GPC), glycoprotein precursor domain of JUNV (JUNV-GPC), glycoprotein precursor domain of GTOV (GTOV-GPC), glycoprotein precursor domain of WWAV (WWAV-GPC), or glycoprotein precursor domain of PICV (PICV-GPC). Preferably, the fragments comprise a fragment of LASV-GPC including residues 441-449, a fragment of LMCV-GPC including residues 447-455, a fragment of MACV-GPC including residues 444-452, a fragment of JUNV-GPC including residues 429-437, a fragment of GTOV-GPC including residues 427-435, a fragment of WWAV-GPC including residues 428-436, or a fragment of PICV-GPC including residues 455-463.

In one preferred embodiment, the DNA vaccine consists essentially of one of said coding sequences—a single agent or monovalent vaccine. In another preferred embodiment, the DNA vaccine consists essentially of at least two of said coding sequences—a multiple agent or multivalent vaccine. Preferably, the monovalent or multivalent vaccine includes the disclosed LASV-GPC, and more preferably SEQ ID NOS: 1 or 2, or nucleotide encoding sequences encoding SEQ ID NOS:4 or 5.

In some embodiments, the provided DNA vaccines further comprise an adjuvant selected from the group consisting of IL-12, IL-15, IL-28, or RANTES.

In one aspect of the invention, there are provided methods of inducing a protective immune response against an arenavirus comprising administering a DNA vaccine provided herein, and electroporating said subject. In some embodiments, the electroporating step comprises delivering an electroporating pulse of energy to a site on said subject that administration step occurred. Preferably, the administration step and electroporating step both occur in an intradermal layer of said subject.

The disclosed invention relates to novel DNA vaccine candidates that generate a protective immune response in a subject against one or in some cases multiple arenaviruses (LASV, LCMV, MACV, JUNV, GTOV, WWAV, and PICV) encompassing both old and new world pathogens.

The provided vaccines are comprised of: AV GPC domain DNA immunogens to increase diversity of immune responses and cross-protection against multiple related but divergent viruses. Further described herein are genetically optimized immunogens, in particular the optimized GPC domains, for the arena viruses that are able to target a broader spectrum of pathogens. One embodiment of the vaccine is an optimized LASV encoding sequence, which can additionally include vaccines targeting the LASV, LCMV, MACV, JUNV, GTOV, WWAV, and PICV viruses, and preferably MACV and JUNV viruses, to achieve a multi-agent formulation.

The vaccines can be combined with highly innovative manufacturing processes and optimized vaccine formulations to enhance the potency of multi-agent formulations. Traditionally, DNA has only been able to be manufactured at 2-4 mg/mL in concentration. This physical limitation makes it difficult to combine DNA plasmids targeting multiple antigens at high enough dose levels to achieve protective efficacy. By utilizing a proprietary manufacturing process such as that described in U.S. Pat. No. 7,238,522 and US Patent Publication No. 2009-0004716, which are incorporated herein in their entirety, DNA plasmids can be manufactured at >10 mg/mL concentration with high purity. This high concentration formulation is also beneficial for efficient delivery at a small injection volume (0.1 mL) such as for conventional ID injection.

The vaccines can be also be combined with highly innovative and efficient electroporation (EP) based DNA delivery systems to increase the potency of the injected DNA vaccine. The EP delivery systems with shallow electroporation depths and low/transient electric parameters make the new devices considerably more tolerable for prophylactic applications and mass vaccinations.

This DNA vaccine combined with the provided manufacturing processes and electroporation delivery devices can provide the following benefits, among others:

No vector induced responses—repeat boosts; multiple/combination vaccines

Greater potency than viral vectors in primates and in humans

Manufacturing advantages

Provided herein are details of a single agent LASV vaccine candidate that has been shown to elicit in a subject 100% protection from lethality in a guinea pig and a non-human primate challenge model. The LASV vaccine candidate was shown in a non-human primate model to facilitate the clinical translation of this vaccine approach. Such success against two different challenge models has not been achieved previously in the literature with any other arenavirus vaccine candidate—vectored or non-vectored.

The LASV vaccine candidate is a multi-agent candidate vaccine that targets both old world and new world viruses. The GPC antigen (the immunogenic component of the viruses) is not highly conserved across LASV, MACV, and JUNV with homologies ranging from 42-71% across the different arenavirus subtypes (LASV-MACV/JUNV; and MACV-JUNV respectively) and 2-10% differences amongst sequences within the different subtypes. Thus developing a multi-agent vaccine is not obvious and fraught with several technical challenges.

The vaccine candidates provided herein have optimized the candidate GPC vaccines for each of the targeted virus subtypes so that they are individually effective against the respective strains (for example, LASV, JUNV, MACV) and collectively cross-protective against these and other arenavirus strains. The vaccine candidates are manufactured so that the plasmid components are at high concentrations (>10 mg/mL). The components of the vaccine candidate can be combined for delivery with EP. EP delivery has been shown to improve DNA transfection and gene expression efficiency by over 1000× and improve immunogenicity and efficacy by over 10-100× relative to DNA delivery without EP. The multiple DNA vaccine-low injection volume-EP delivery makes this approach especially suitable for prophylactic vaccinations and, in particular, multiagent vaccine delivery.

The DNA vaccine approach described herein holds a distinct safety advantage over other competing live attenuated/killed virus approaches and other vector based approaches (Ad5, MVA, YF) because the DNA vaccine is non-replicating, does not integrate into the genome, and unlike vectors, does not give rise to anti-vector serology which can further limit the potency of vectored vaccines. DNA vaccines have now been delivered to several thousands of human subjects across a few hundred different vaccine trials with little of note from a safety stand-point. Together with EP delivery, DNAEP vaccines (HIV, HPV, influenza, HCV, prostate cancer, melanoma) have been delivered to over 150+ subjects and over 350+ vaccinations via either intramuscular or intradermal routes and the safety profiles have been unremarkable.

In one embodiment, the vaccine candidate can have the following specifications:

| No. | Characteristic | Target | Acceptable | Rationale |
|-----|----------------|--------|------------|-----------|
| 1.  | Vaccine target | Multi-agent (LASV, LCMV, MACV, JUNV, GTOV, WWAV, and PICV) | Single agent | deploy 2, 3 or more single agent vaccines if efficacy criteria are met |

-continued

| No. | Characteristic | Target | Acceptable | Rationale |
|---|---|---|---|---|
| 2. | Vaccine formulation and delivery | 0.1 mL; ID delivery to single site; Target a high dose (1 mg/plasmid for single agent; 0.3 mg/plasmid for multiple agent) | 0.2 mL; ID delivery to two sites | Clear unmet need and lack of effective countermeasures can make two vaccinations acceptable for biodefense use |
| 3. | Choice of adjuvants | Adjuvant can be optionally added to the vaccine formulation | Either of IL-12, IL-28, or RANTES is included | An adjuvant would be acceptable if it conferred any benefits such as - enhanced immunogenicity, cross-protective responses, and/or dose-sparing characteristics to the vaccine formulation |
| 4. | Vaccine efficacy | 90-100% protection from lethality in a guinea pig challenge model against all three strains | 90-100% protection from lethality in a guinea pig challenge model against a single strain | deploy 3 single agent vaccines if efficacy criteria are met |
| 5. | Vaccine immunogenicity | Demonstration of vaccine induced antigen specific cellular and humoral responses in NHP model IFNg ELISpot, ICS, killing fn. (perforin, T-bet, granzyme); ELISA, NAb | Demonstration of vaccine induced antigen specific cellular or humoral responses in guinea pig model | No correlates of protection are known for AV. Characterization of both cellular and humoral responses for purposes of understanding magnitude and breadth of immune responses achievable in NHP. |

Challenges will be carried out in guinea pigs (Strain 13) and *cynomolgus macaques*. As noted in the research section, these are both established models for arenavirus challenge.

In some embodiments the vaccine candidates will contain all 2 or more vaccine candidates (LASV, LCMV, MACV, JUNV, GTOV, WWAV, and PICV), which can confer cross-protection; while in other embodiments, there is a combination of only two vaccine candidates, and more preferably examples of two-one old world and one new world plasmids, e.g. LASV and either JUNV or MACV to confer protection against all multiple strains of AV. In one example, the DNA vaccine comprises two DNA vaccine plasmids (LASV+JUNV/MACV). In another example, the DNA vaccine comprises a vaccine candidate and a cytokine plasmid. In another example, the DNA vaccine comprises three plasmid vaccine candidates, including LASV, JUNV, and MACV.

There are some embodiments where the vaccine candidates also include molecular adjuvants, e.g., IL-12 and IL-28, and RANTES. The adjuvants can increase breadth of immune responses, their magnitude or alter the immune phenotype of the vaccine to confer additional benefit to the vaccine such as: improved cross-strain efficacy (breadth) and/or 100% efficacy at a lower dose (potency).

In some embodiments, the vaccine candidate is a single plasmid targeting LASV. This single plasmid candidate has been shown to be highly effective in protecting guinea pigs and non-human primate ("NHP") from a lethal challenge.

DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Adjuvant

"Adjuvant" as used herein means any molecule added to the DNA vaccines described herein to enhance the immunogenicity of the antigens encoded by the DNA constructs, which makes up the DNA vaccines, and the encoding nucleic acid sequences described hereinafter.

Coding Sequence

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to who the nucleic acid is administered.

Complement

"Complement" or "complementary" as used herein means a nucleic acid can mean Watson-Crick (e.g., A-T/U and C-G) or Hoogsteen base pairing between nucleotides or nucleotide analogs of nucleic acid molecules.

Electroporation

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

Fragment

"Fragment" as used herein with respect to nucleic acid sequences means a nucleic acid sequence or a portion thereof, that encodes a polypeptide capable of eliciting an immune response in a mammal that cross reacts with a arenavirus GPC antigen. The fragments can be DNA fragments selected from at least one of the various nucleotide sequences that encode the consensus amino acid sequences and constructs comprising such sequences. DNA fragments can comprise coding sequences for the immunoglobulin leader such as IgE or IgG sequences. DNA fragments can encode the protein fragments set forth below.

"Fragment" with respect to polypeptide sequences means a polypeptide capable of eliciting an immune response in a mammal that cross reacts with a arenavirus antigen, including, e.g. Lassa virus (LASV), choriomeningitis virus (LCMV), Junin virus (JUNV), Machupo virus (MACV), lyphocytic Guanarito virus (GTOV), White-water Arroyo virus (WWAV), and Pichinde virus (PICV).

The LASV glycoprotein precursor (LASV-GPC) sequence is about 491 amino acids, and preferably codon optimized. Fragments of LASV-GPC may comprise at least 90%, 91%, 92%, 93%, 94%, 95%, 96%, 97%, 98%, or 99% of the LASV-GPC, and preferably fragments containing residues 441 to 449 of the GPC region. In some embodiments, fragments of LASV-GPC comprise at least 90%, 91%, 92%, 93%, 94%, 95%, 96%, 97%, 98%, or 99% of SEQ ID NO:4 or 5.

The LCMV glycoprotein precursor (LCMV-GPC) sequence is about 498 amino acids, and preferably codon optimized—see NCBI accession number NP_694851, which is incorporated herein in its entirety. Fragments of LCMV-GPC may comprise at least 90%, 91%, 92%, 93%, 94%, 95%, 96%, 97%, 98%, or 99% of LCMV-GPC, and preferably fragments contain residues 447-455.

The JUNV glycoprotein precursor (JUNV-GPC) sequence is about 485 amino acids, and preferably codon optimized—see NCBI accession number BAA00964, which is incorporated herein in its entirety. Fragments of JUNV-GPC may comprise at least 90%, 91%, 92%, 93%, 94%, 95%, 96%, 97%, 98%, or 99% of JUNV-GPC, and preferably fragments contain residues 429-437.

The MACV glycoprotein precursor (MACV-GPC) sequence is about 496 amino acids, and preferably codon optimized—see NCBI accession number AAN05425, which is incorporated herein in its entirety. Fragments of MACV-GPC may comprise at least 90%, 91%, 92%, 93%, 94%, 95%, 96%, 97%, 98%, or 99% of MACV-GPC, and preferably fragments contain residues 444-452.

The GTOV glycoprotein precursor (GTOV-GPC) sequence is about 496 amino acids, and preferably codon optimized—see NCBI accession number AAN05423, which is incorporated herein in its entirety. Fragments of GTOV-GPC may comprise at least 90%, 91%, 92%, 93%, 94%, 95%, 96%, 97%, 98%, or 99% of GTOV-GPC, and preferably fragments contain residues 427-435.

The WWAV glycoprotein precursor (WWAV-GPC) sequence is about 496 amino acids, and preferably codon optimized—see NCBI accession number AAK60497, which is incorporated herein in its entirety. Fragments of WWAV-GPC may comprise at least 90%, 91%, 92%, 93%, 94%, 95%, 96%, 97%, 98%, or 99% of WWAV-GPC, and preferably fragments contain residues 428-436.

The PICV glycoprotein precursor (PICV-GPC) sequence is about 496 amino acids, and preferably codon optimized—see NCBI accession number AAC32281, which is incorporated herein in its entirety. Fragments of PICV-GPC may comprise at least 90%, 91%, 92%, 93%, 94%, 95%, 96%, 97%, 98%, or 99% of PICV-GPC, and preferably fragments contain residues 455-463.

Genetic Construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

Homology

Homology of multiple sequence alignments and phylogram were generated using ClustalW software.

Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

Immune Response

"Immune response" as used herein means the activation of a host's immune system, e.g., that of a mammal, in response to the introduction of antigen such as a arenavirus antigen. The immune response can be in the form of a cellular or humoral response, or both.

Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

Operably Linked

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, or 1440 or more nucleotides or amino acids, or that the two sequences hybridize under stringent hybridization conditions.

Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, or 1440, or more nucleotides or amino acids, or with respect to nucleic acids, if the first sequence is substantially complementary to the complement of the second sequence.

Subtype or Serotype

"Subtype" or "serotype": as used herein, interchangeably, and in reference to arenavirus antigens, means genetic variants of an arenavirus antigen such that one subtype (or variant) is recognized by an immune system apart from a different subtype.

Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retains protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Vector

"Vector" as used herein means a nucleic acid sequence containing an origin of replication. A vector can be a vector, bacteriophage, bacterial artificial chromosome or yeast artificial chromosome. A vector can be a DNA or RNA vector. A vector can be a self-replicating extrachromosomal vector, and preferably, is a DNA plasmid.

Excipients and Other Components of the Vaccine

The vaccine can further comprise other components such as a transfection facilitating agent, a pharmaceutically acceptable excipient, an adjuvant. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent can be a polyanion, polycation, including poly-L-glutamate (LGS), or lipid. The transfection facilitating agent can be poly-L-glutamate. The poly-L-glutamate can be present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA plasmid vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine can further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Method of Vaccination

Provided herein is a method of vaccinating a subject. The method uses electroporation as a mechanism to deliver the vaccine. The electroporation can be carried out via a minimally invasive device.

AV GPC Antigens, Codon Optimized

The LASV glycoprotein precursor (LASV-GPC) sequence is about 491 amino acids, and preferably codon optimized. Fragments of LASV-GPC may comprise at least 90%, 91%, 92%, 93%, 94%, 95%, 96%, 97%, 98%, or 99% of the LASV-GPC, and preferably fragments containing residues 441 to 449 of the GPC region. In some embodiments, fragments of LASV-GPC comprise at least 90%, 91%, 92%, 93%, 94%, 95%, 96%, 97%, 98%, or 99% of SEQ ID NO:4 or 5.

The LCMV glycoprotein precursor (LCMV-GPC) sequence is about 498 amino acids, and preferably codon optimized—see NCBI accession number NP_694851, which is incorporated herein in its entirety. Fragments of LCMV-GPC may comprise at least 90%, 91%, 92%, 93%, 94%, 95%, 96%, 97%, 98%, or 99% of LCMV-GPC, and preferably fragments contain residues 447-455.

The JUNV glycoprotein precursor (JUNV-GPC) sequence is about 485 amino acids, and preferably codon optimized—see NCBI accession number BAA00964, which is incorporated herein in its entirety. Fragments of JUNV-GPC may comprise at least 90%, 91%, 92%, 93%, 94%, 95%, 96%, 97%, 98%, or 99% of JUNV-GPC, and preferably fragments contain residues 429-437.

The MACV glycoprotein precursor (MACV-GPC) sequence is about 496 amino acids, and preferably codon optimized—see NCBI accession number AAN05425, which is incorporated herein in its entirety. Fragments of MACV-GPC may comprise at least 90%, 91%, 92%, 93%, 94%, 95%, 96%, 97%, 98%, or 99% of MACV-GPC, and preferably fragments contain residues 444-452.

The GTOV glycoprotein precursor (GTOV-GPC) sequence is about 496 amino acids, and preferably codon optimized—see NCBI accession number AAN05423, which is incorporated herein in its entirety. Fragments of GTOV-GPC may comprise at least 90%, 91%, 92%, 93%, 94%, 95%, 96%, 97%, 98%, or 99% of GTOV-GPC, and preferably fragments contain residues 427-435.

The WWAV glycoprotein precursor (WWAV-GPC) sequence is about 496 amino acids, and preferably codon optimized—see NCBI accession number AAK60497, which is incorporated herein in its entirety. Fragments of WWAV-GPC may comprise at least 90%, 91%, 92%, 93%, 94%, 95%, 96%, 97%, 98%, or 99% of WWAV-GPC, and preferably fragments contain residues 428-436.

The PICV glycoprotein precursor (PICV-GPC) sequence is about 496 amino acids, and preferably codon optimized—see NCBI accession number AAC32281, which is incorporated herein in its entirety. Fragments of PICV-GPC may comprise at least 90%, 91%, 92%, 93%, 94%, 95%, 96%, 97%, 98%, or 99% of PICV-GPC, and preferably fragments contain residues 455-463.

Nucleotide Sequences—Encoding Sequences and Constructs and Plasmids

The LASV glycoprotein precursor (LASV-GPC) nucleotide encoding sequence is about 1476 nucleotides, and preferably codon optimized. Encoding sequences of immunogenic fragments of LASV-GPC may comprise at least 90%, 91%, 92%, 93%, 94%, 95%, 96%, 97%, 98%, or 99% of the encoded LASV-GPC, and preferably fragments containing residues 441 to 449 of the GPC region. In some embodiments, the encoding sequences of LASV-GPC are SEQ ID NOs.:1 and 2. In some embodiments, encoding sequences of fragments of LASV-GPC comprise at least 90%, 91%, 92%, 93%, 94%, 95%, 96%, 97%, 98%, or 99% of SEQ ID NO:4 or 5. In some embodiments, encoding sequences of fragments of LASV-GPC comprise at least 90%, 91%, 92%, 93%, 94%, 95%, 96%, 97%, 98%, or 99% of SEQ ID NO:1 or 2.

The LCMV glycoprotein precursor (LCMV-GPC) nucleotide encoding sequence is about 1494 nucleotides, and preferably codon optimized—see NCBI accession number NP_694851, which is incorporated herein in its entirety. Encoding sequences of immunogenic fragments of LCMV-GPC may comprise at least 90%, 91%, 92%, 93%, 94%, 95%, 96%, 97%, 98%, or 99% of LCMV-GPC, and preferably fragments contain residues 447-455.

The JUNV glycoprotein precursor (JUNV-GPC) nucleotide encoding sequence is about 1455 nucleotides, and preferably codon optimized—see NCBI accession number BAA00964, which is incorporated herein in its entirety. Encoding sequences of immunogenic fragments of JUNV-GPC may comprise at least 90%, 91%, 92%, 93%, 94%, 95%, 96%, 97%, 98%, or 99% of JUNV-GPC, and preferably fragments contain residues 429-437.

The MACV glycoprotein precursor (MACV-GPC) nucleotide encoding sequence is about 1488 nucleotides, and preferably codon optimized—see NCBI accession number AAN05425, which is incorporated herein in its entirety. Encoding sequences of immunogenic fragments of MACV-GPC may comprise at least 90%, 91%, 92%, 93%, 94%, 95%, 96%, 97%, 98%, or 99% of MACV-GPC, and preferably fragments contain residues 444-452.

The GTOV glycoprotein precursor (GTOV-GPC) nucleotide encoding sequence is about 1488 nucleotides, and preferably codon optimized—see NCBI accession number AAN05423, which is incorporated herein in its entirety. Encoding sequence of immunogenic fragments of GTOV-GPC may comprise at least 90%, 91%, 92%, 93%, 94%, 95%, 96%, 97%, 98%, or 99% of GTOV-GPC, and preferably fragments contain residues 427-435.

The WWAV glycoprotein precursor (WWAV-GPC) nucleotide encoding sequence is about 1488 nucleotides, and preferably codon optimized—see NCBI accession number AAK60497, which is incorporated herein in its entirety. Encoding sequences of immunogenic fragments of WWAV-GPC may comprise at least 90%, 91%, 92%, 93%, 94%, 95%, 96%, 97%, 98%, or 99% of WWAV-GPC, and preferably fragments contain residues 428-436.

The PICV glycoprotein precursor (PICV-GPC) nucleotide encoding sequence is about 1488 nucleotides, and preferably codon optimized—see NCBI accession number AAC32281, which is incorporated herein in its entirety. Encoding sequences of immunogenic fragments of PICV-GPC may comprise at least 90%, 91%, 92%, 93%, 94%, 95%, 96%, 97%, 98%, or 99% of PICV-GPC, and preferably fragments contain residues 455-463.

Provided herein are genetic constructs that can comprise a nucleic acid sequence that encodes the AV GPC antigen disclosed herein including immunogenic fragments thereof. The genetic construct can be present in the cell as a functioning extrachromosomal molecule. The genetic construct can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing an antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding an antigen, which the transformed host cell is cultured and maintained under conditions wherein expression of the antigen takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding an antigen and can further comprise an initiation codon, which can be upstream of the antigen coding sequence, and a stop codon, which can be downstream of the antigen coding sequence. The initiation and termination codon can be in frame with the antigen coding sequence. The vector can also comprise a promoter that is operably linked to the antigen coding sequence. The promoter operably linked to the antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the AV GPC protein coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the AV GPC protein coding sequence. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pWRG7077 (see Schmaljohn et al., infra), pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993. Based upon the sequence of pVAX1 available from Invitrogen, the following mutations were found in the sequence of pVAX1 that was used as the backbone for plasmids 1-6 set forth herein:

| | | |
|---|---|---|
| C > G | 241 | in CMV promoter |
| C > T | 1942 | backbone, downstream of the bovine growth hormone polyadenylation signal (bGHpolyA) |
| A > — | 2876 | backbone, downstream of the Kanamycin gene |
| C > T | 3277 | in pUC origin of replication (Ori) high copy number mutation (see Nucleic Acid Research 1985) |
| G > C | 3753 | in very end of pUC Ori upstream of RNASeH site |

Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The AV GPC coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

Pharmaceutical Compositions

Provided herein are pharmaceutical compositions according to the present invention, also denoted as DNA vaccines herein, which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanograms to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

Provided herein is a vaccine capable of generating in a mammal an protective immune response against one or more AV. The vaccine can comprise the genetic construct as discussed herein.

While not being bound by scientific theory, the vaccine can be used to elicit an immune response (humoral, cellular, or both) broadly against one or more types of AV.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the AV GPC protein. The RNA vaccine can be introduced into the cell.

The vaccine can be a recombinant vaccine comprising the genetic construct or antigen described herein. The vaccine can also comprise one or more AV GPC core protein in the form of one or more protein subunits, one or more killed viral particles comprising one or more AV GPC protein, or one or more attenuated viral particles comprising one or more AV GPC protein. The attenuated vaccine can be attenuated live vaccines, killed vaccines and vaccines that use recombinant vectors to deliver foreign genes that encode one or more AV GPC protein, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine can comprise vectors and/or proteins directed to multiple AVs from multiple particular regions in the world. The vaccine provided can be used to induce immune responses including therapeutic or prophylactic immune responses. Antibodies and/or killer T cells can be generated which are directed to the AV GPC protein, and also broadly across multiple AV viruses. Such antibodies and cells can be isolated.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

Adjuvants

The pharmaceutically acceptable excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. Preferably, the adjuvants are IL12, IL15, IL28, and RANTES Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

Methods of Delivery

Provided herein is a method for delivering the pharmaceutical formulations, preferably vaccines, for providing genetic constructs and proteins of the AV GPC protein which comprise epitopes that make them particular effective immunogens against which an immune response to AV viral infections can be induced. The method of delivering the vaccine, or vaccination, can be provided to induce a therapeutic and/or prophylactic immune response. The vaccination process can generate in the mammal an immune response against a plurality of AV viruses. The vaccine can be delivered to an individual to modulate the activity of the mammal's immune system and enhance the immune response. The delivery of the vaccine can be the transfection of the AV GPC antigen as a nucleic acid molecule that is expressed in the cell and delivered to the surface of the cell upon which the immune system recognized and induces a cellular, humoral, or cellular and humoral response. The delivery of the vaccine can be used to induce or elicit and immune response in mammals against a plurality of AV viruses by administering to the mammals the vaccine as discussed herein. Upon delivery of the vaccine to the mammal, and thereupon the vector into the cells of the mammal, the transfected cells will express and secrete AV GPC protein. These secreted proteins, or synthetic antigens, will be recognized as foreign by the immune system, which will mount an immune response that can include: antibodies made against the antigens, and T-cell response specifically against the antigen. In some examples, a mammal vaccinated with the vaccines discussed herein will have a primed immune system and when challenged with an AV viral strain, the primed immune system will allow for rapid clearing of subsequent AV viruses, whether through the humoral, cellular, or both. The vaccine can be delivered to an individual to modulate the activity of the individual's immune system thereby enhancing the immune response.

The vaccine can be delivered in the form of a DNA vaccine and methods of delivering a DNA vaccines are described in U.S. Pat. Nos. 4,945,050 and 5,036,006, which are both incorporated fully by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

Routes of Administration

The vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The AV GPC antigen can be delivered via DNA injection and along with in vivo electroporation.

Electroporation

Administration of the vaccine via electroporation of the plasmids of the vaccine can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid. Examples of electroporation devices and electroporation methods that can facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety. U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Publication 2005/0052630 is hereby incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

Method of Preparing Vaccine

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description.

Animal Study—Guinea Pig

Strain 13 guinea pigs (*Cavia porcellus*) were divided into 4 groups of 6 animals each (pilot study) or 7 groups of either 8 or 5 animals each (follow-on study). Animals were anesthetized then administered either an authentic (LASV-GPC—either SEQ ID NO: 1 (optimized) or SEQ ID NO:3 (non-optimized)) or mock (empty plasmid) vaccination of 12 μg (gene gun or GG) or 100 μg (via intramuscular electroporation device (IM EP), the minimally invasive intradermal device (MID), or the noninvasive device (NINV)) DNA at 3 week intervals. Four weeks after the final vaccination, viral infections were carried out under biosafety level (BSL)-4 conditions. Each animal was administered a single s.c. dose of 1000 pfu of LASV. Animals were observed daily for disease progression. Blood samples were taken on days −7 or 0, 7, 14, 21 and 29 or 32 postinfection. Animals were euthanized when moribund. Serum samples were analyzed for viremia and blood chemistry values. Necropsies were performed on each animal, and tissues were analyzed for LASV-specific histopathological and immunohistochemical analysis.

Animal Study—Nonhuman Primate

*Cynomolgus macaques* (*Macaca fasicularis*) were divided into 2 groups of 4 animals each. Animals were anesthetized then administered either an authentic or mock vaccination of 1 mg DNA (SEQ ID NO:2) at 3 week intervals. Four weeks after the final vaccination, viral infections were carried out under BSL-4 conditions. Each animal was administered a single i.m. dose of 1000 pfu of LASV. Animals were observed daily for disease progression. Blood samples were taken at days 0, 3, 6, 10, 14, 21, 28 and 45 postinfection. Animals were euthanized when moribund. Blood samples were analyzed for CBC, blood chemistry and serum viremia.

Analysis of Viremia

Vero cells, seeded in 6-well cell culture plates, were adsorbed with gentle rotation at 37° C., 5% $CO_2$ with 10-fold serial dilutions of serum for 1 h, then an overlay of 0.8% agarose in EBME with 10% fetal bovine serum was applied to each well. Cells were then incubated at 37° C., 5% $CO_2$ for 4 days, then stained with neutral red (Invitrogen, Carlsbad, Calif.). Plaques were counted and recorded.

Blood Chemistry Analysis

Primate serum samples were analyzed for GLU, CRE, UA, CA, ALB, TP, ALT, AST, (ALP), TBIL, GGT, and AMY via the General Chemistry 13-panel rotor on a Piccolo Blood Chemistry Analyzer Abaxis). Guinea pig samples were analyzed for the above on Comprehensive Metabolic Panel via an Abaxis VetScan Blood Chemistry Analyzer Complete Blood Counts For the primate study, an approximate volume of 25 ul whole EDTA blood was analyzed on a Hemavet Instrument (Drew Scientific).

Pathological Analysis of Tissues

Tissues were embedded in paraffin, sectioned and stained with hematoxylin and eosin. Immunohistochemistry was performed using a LASV-specific monoclonal antibody and a commercially available kit (Envision System; DAKO, Carpinteria, Calif.). Tissues were deparaffinization, blocked, then incubated with primary antibody and secondary antibodies, then counterstained with hematoxylin.

Pathological Analysis of Tissues

Tissues were embedded in paraffin, sectioned and stained with hematoxylin and eosin. Immunohistochemistry was performed using a LASV-specific monoclonal antibody and a commercially available kit (Envision System; DAKO, Carpinteria, Calif.). Tissues were deparaffinization, blocked, then incubated with primary antibody and secondary antibodies, then counterstained with hematoxylin.

Generation of LASV DNA

A LASV DNA vaccine was generated by cloning cDNA encoding glycoprotein precursor (GPC) gene of LASV (Josiah strain) into the plasmid vector pWRG7077 as described earlier (Schmaljohn et al., J. Vir. 71, 9563-9569 (1997)). The LASV-GPC gene was cloned into NotI/BgIII restriction site. The expression was under control of CMV promoter.

The protective efficacy of the vaccine was tested by intramuscular (IM) EP delivery to and challenge of guinea pigs, which develop a hemorrhagic disease similar to that observed in nonhuman primates (NHP) and humans. The guinea pigs (6 per group) received 50 µg of the DNA vaccine (comprising SEQ ID NO:3) three times at 3- to 4-week intervals by intramuscular (IM) EP, or ~5 µg by gene gun (GG). About 4-weeks after vaccination, the guinea pigs were challenged by intraperitoneal (IP) administration of 1000 plaque forming units (pfu) of LASV, a standard lethal challenge dose. All of the control guinea pigs succumbed to LASV infection whereas 83% of vaccinated animals survived, and the single animal that died showed a delayed time to death. Neutralizing antibodies to LASV were detected after challenge in the vaccinated, but not the control guinea pigs, indicating that a priming response was elicited by the DNA vaccine (data not shown).

Figure 1:
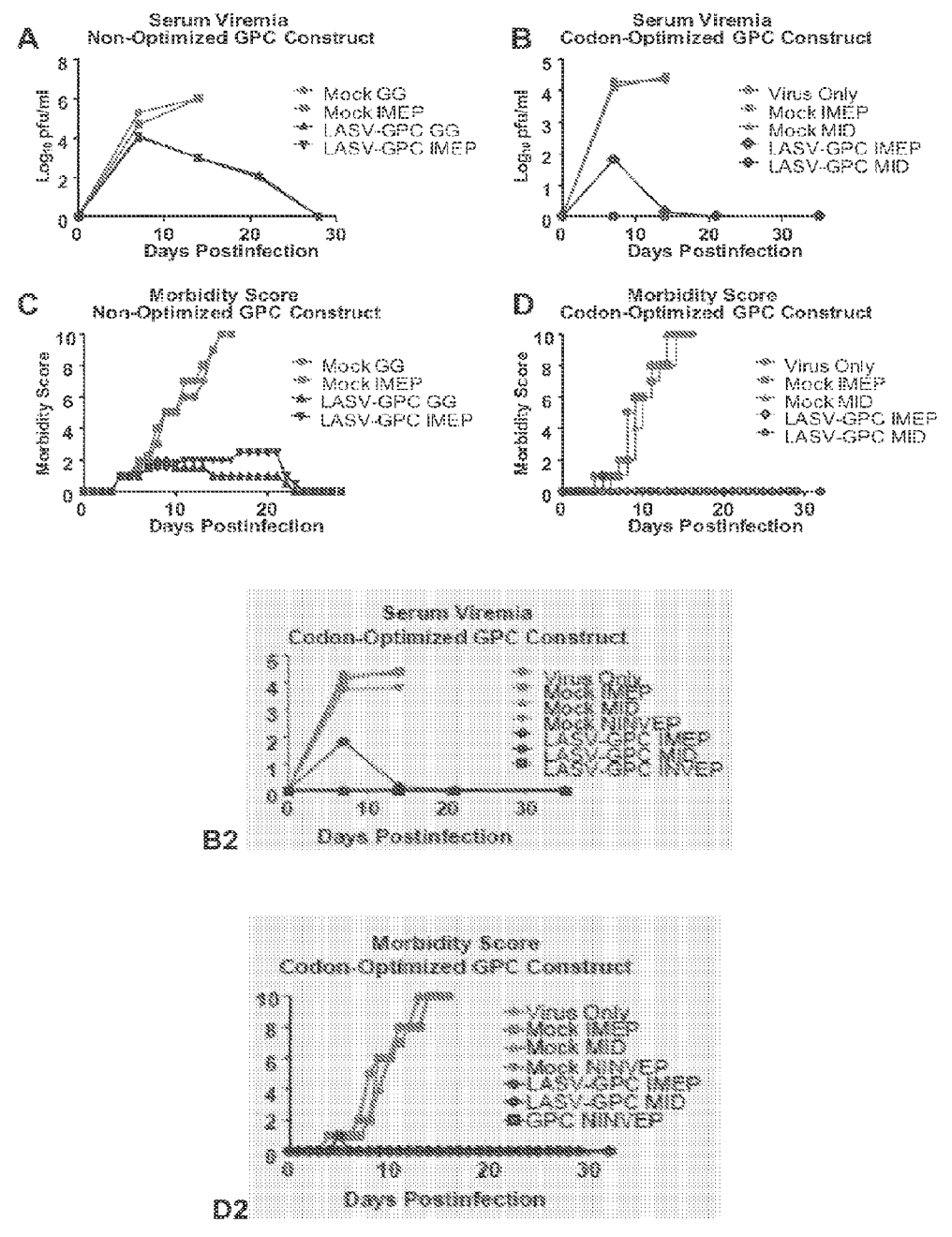

Although this guinea pig study demonstrated that IM EP with the LASV DNA vaccine could elicit protective immunity, the challenged animals did develop fevers and showed mild clinical signs of disease (FIG. 1A, 1C); thus, further improvements to the vaccine construct and intradermal delivery methods were sought. Toward this goal, the LASV GPC DNA vaccine was optimized to maximize mammalian codon availability and to remove viral elements shown to compromise expression. This optimized vaccine (comprising SEQ ID NO:1) was tested in Strain 13 guinea pigs (8 per group), which were vaccinated with 50 µg of DNA three times at 3-4 week intervals, using an intramuscular electroporation device (IM EP) with revised parameters, with the minimally invasive intradermal device (MID), or the non-invasive device (NINV). The (MID) has an electrode spacing is triangular in shape with 3 mm separating electrodes on one side, and 5 mm separating electrodes on other two sides. The NINV has electrode array in a 4×4 pattern that make contact with skin surface without penetrating skin (or alternatively entering skin into stratum corneum).

After challenge, all guinea pigs vaccinated with the empty plasmid or those that received no vaccine became febrile, displayed signs of illness, lost weight and succumbed to infection between days 15 and 18 after challenge (FIG. 1). In contrast, all of the guinea pigs vaccinated with the codon optimized LASV DNA vaccine by any of the EP methods survived challenge. Unlike the pilot study, where the guinea pigs vaccinated with the non-optimized LASV DNA vaccine showed signs of illness, in this study the guinea pigs in both the MID and IM EP groups displayed no signs of disease, remained afebrile, and maintained constant body weights. Mild signs of disease were observed however in some of the guinea pigs that received the LASV DNA vaccine by IM EP, including low fevers and slight viremias, suggesting that dermal electroporation was more efficacious in this study.

FIG. 2 displays the survival curves of guinea pigs (8 per group) vaccinated with codon optimized LASV DNA or with an empty plasmid control using IM or MID dermal EP devices. The guinea pigs were challenged with 1000 pfu of LASV 4-weeks after the last vaccination.

In order to confirm the efficacy and durability of the vaccine and delivery method, a subset of MID EP-vaccinated guinea pigs were selected for a back-challenge experiment. These guinea pigs were held in BSL-4 containment for 120 days, and then were challenged, along with 4 weight-matched naïve guinea pigs with 1000 pfu of LASV. The guinea pigs were observed daily for 30 days following virus infection and were monitored for weight, temperature and disease progression. The vaccinated animals never became ill during the study and survived re-infection (FIG. 3).

Figure 3:
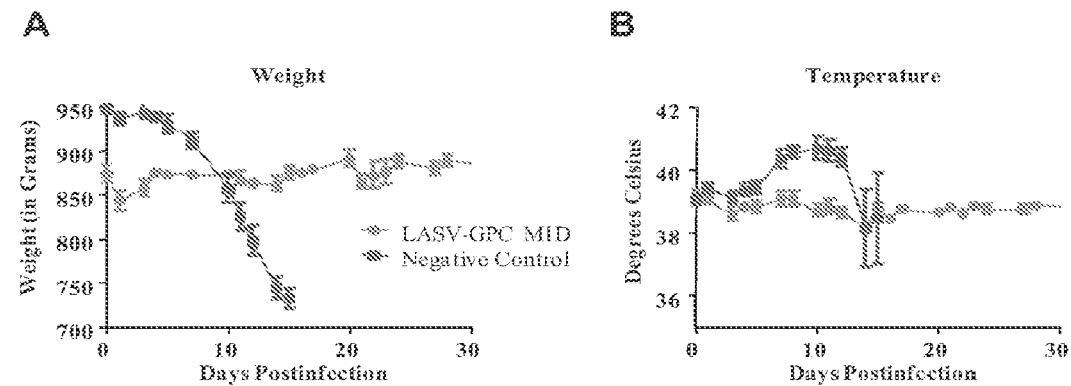
FIGS. 3(A) and 3(B) display weights and temperatures in guinea pigs enrolled in the back challenge study.

FIG. 3 displays the results of a back-challenge experiment of a subset of MID EP-vaccinated guinea pigs with FIG. 3A showing the changes in group body weight and FIG. 3B showing the changes in mean body temperature of groups.

The codon-optimized LASV DNA vaccine (comprising SEQ ID NO:2) delivered by the MID EP in NHPs were further evaluated. The NHP model is the most informative model for assessment of vaccine efficacy, because the disease observed in these animals most closely mimics human disease.

Figure 4:
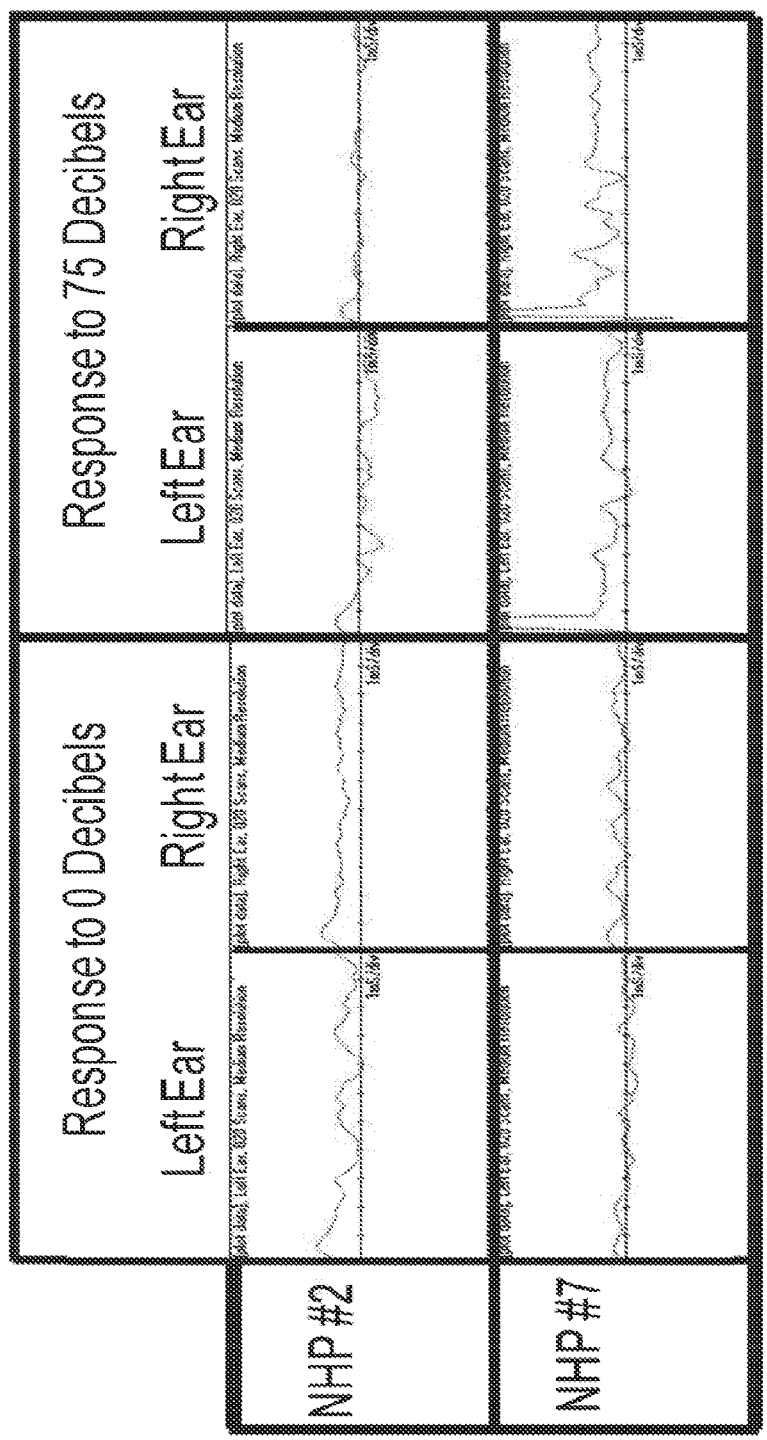
FIG. 4 displays a BAERCOM auditory screening of LASV-GPC or mock-vaccinated monkeys that survived lethal challenge with LASV.

Groups of four NHPs were vaccinated using the MID EP device with 1 mg of the LASV DNA vaccine (comprising SEQ ID NO:2) or 1 mg of empty vector plasmid three times at 3-week intervals and were challenged by IM injection of 1000 pfu of LASV 4-weeks after the final vaccination. Blood samples collected from the NHPs were monitored for CBCs and blood chemistries and the animals were observed twice daily for disease progression. Two of the four control NHPs succumbed to disease during the hemorrhagic window (days 13 and 17 post infection). The other two control NHPs developed neurological symptoms including ataxia and deafness, as indicated by comparing their audiograms generated on the final day of study (45 days post-challenge) to those of LASV DNA-vaccinated NHPs (FIG. 4). Deafness (either unilateral or bilateral) is a well-recognized consequence of LASV infection occurring in approximately 30% of LASV patients, but to our knowledge, this is the first documentation of this disease consequence in NHPs, and can serve as a disease marker.

As shown in FIG. 4, the audiograms for NHP #2 and NHP #7, respectively were vaccinated with empty plasmid or the LASV DNA vaccine. Audiograms from both monkeys with a 0 decibel stimulus show no response. The audiograms for the left and right ears of NHP #2 show no response at 75 decibels, in contrast to the audiograms of NHP #7, which show hearing response patterns.

Although two of the control NHPs survived infection, they remained critically ill throughout the study (day 45 post infection). In contrast, the four LASV DNA-vaccinated NHPs appeared healthy throughout the study, were never febrile, and maintained normal CBC and blood chemistries (FIG. 5).

Figure 5:
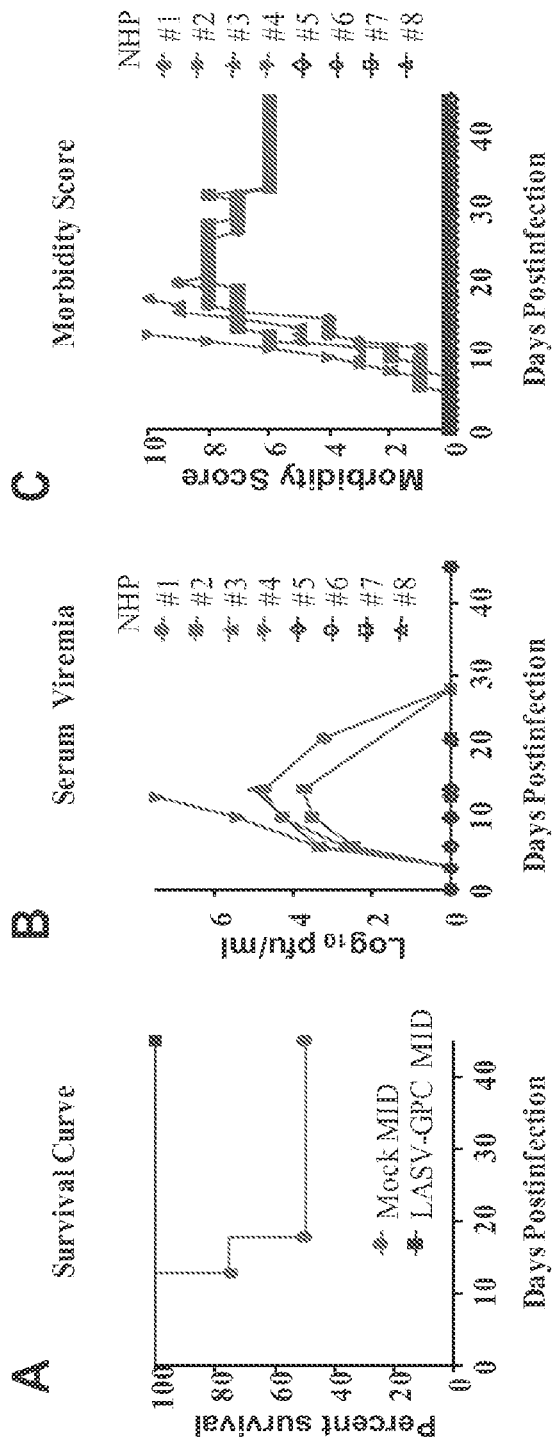
FIGS. 5(A), 5(B), and 5(C) display the survival curve, serum viremia and morbidity score for *cynomolgus macaque* receiving the LASV-GPC (comprising SEQ ID NO:2) or mock (comprising SEQ ID NO:3) DNA vaccine.

FIG. 5 displays the survival, viremia and morbidity scores of NHPs vaccinated with the LASV DNA vaccine or empty plasmid by MID EP and challenged with LASV. FIG. 5A shows all LASV DNA-vaccinated NHPs survived LASV challenge whereas 2 of 4 control NHPs vaccinated with empty plasmid succumbed to infection. FIG. 5B shows all 4 empty plasmid-vaccinated NHPs became viremic, but the 2 surviving NHPs were able to clear virus by 28 days post challenge. The LASV DNA-vaccinated NHPs were aviremic at all timepoints. C. Morbidity score is a measure of how sick the NHPs became during the study. Control animals became critically ill before death. The 2 NHPs that did not die remained chronically ill until the end of the study, never returning to pre-challenge condition. The LASV DNA-vaccinated NHPs never became ill.

Figure 6C:
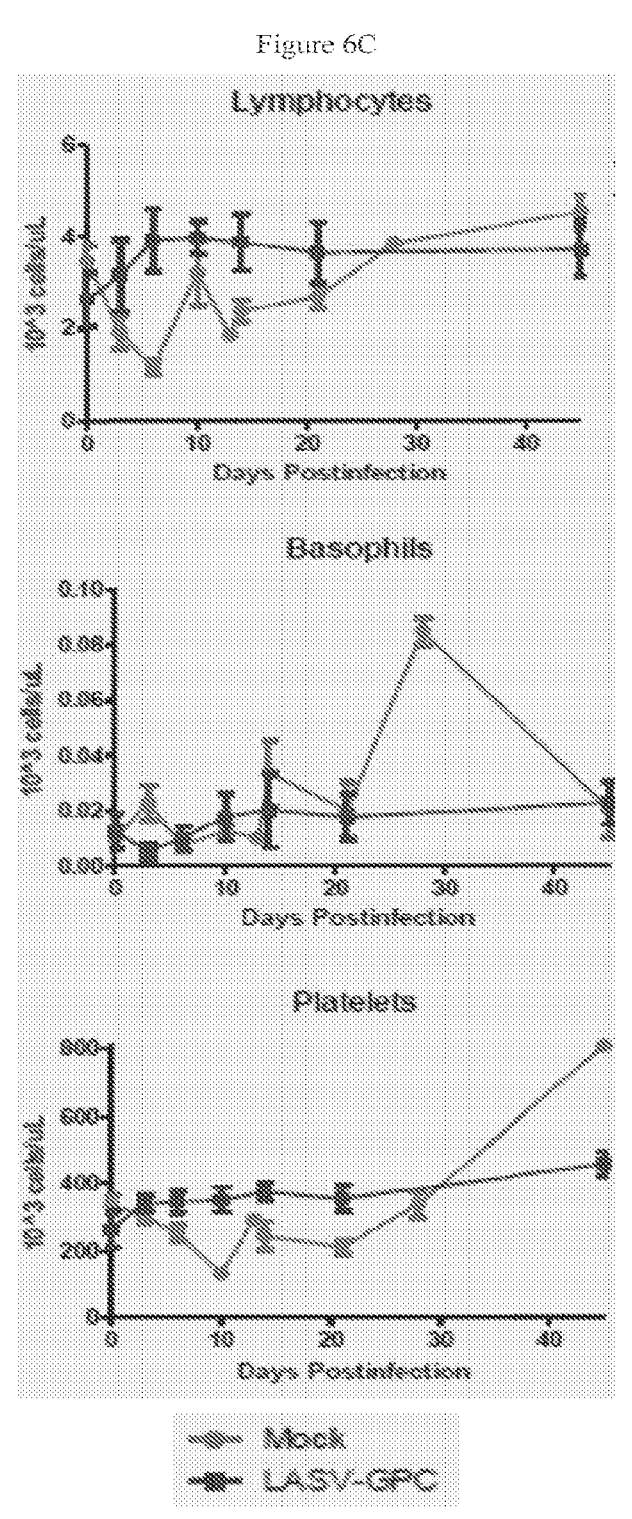

FIG. 6 shows selected blood chemistry values for *cynomolgus* receiving the LASV-GPC (comprising SEQ ID NO:2) or mock DNA vaccine.

Figure 7:
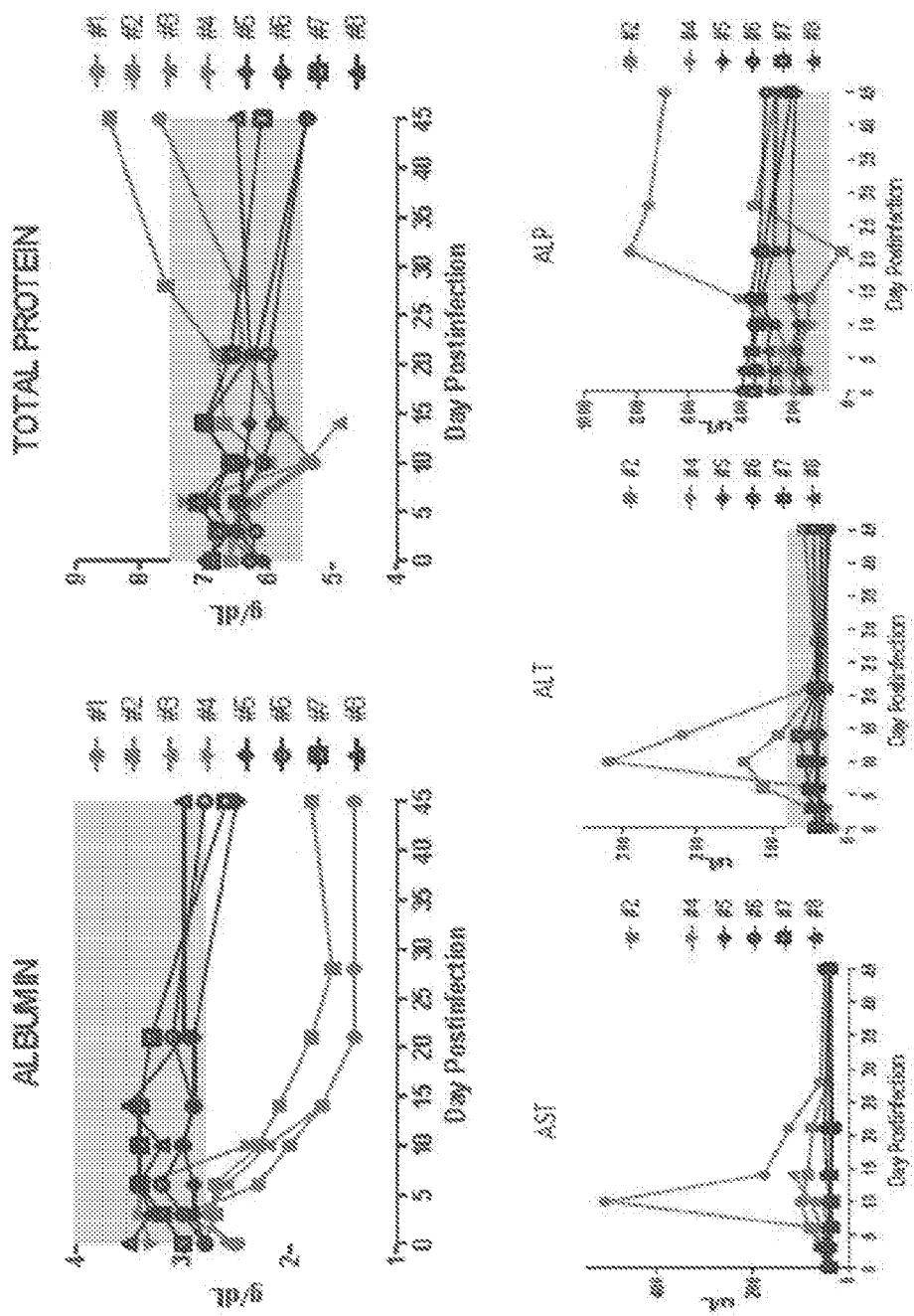
FIG. 7 displays selected hematology values for *cynomolgus* receiving the LASV-GPC (comprising SEQ ID NO:2) or mock (comprising SEQ ID NO:3) DNA vaccine.
Figure 8:
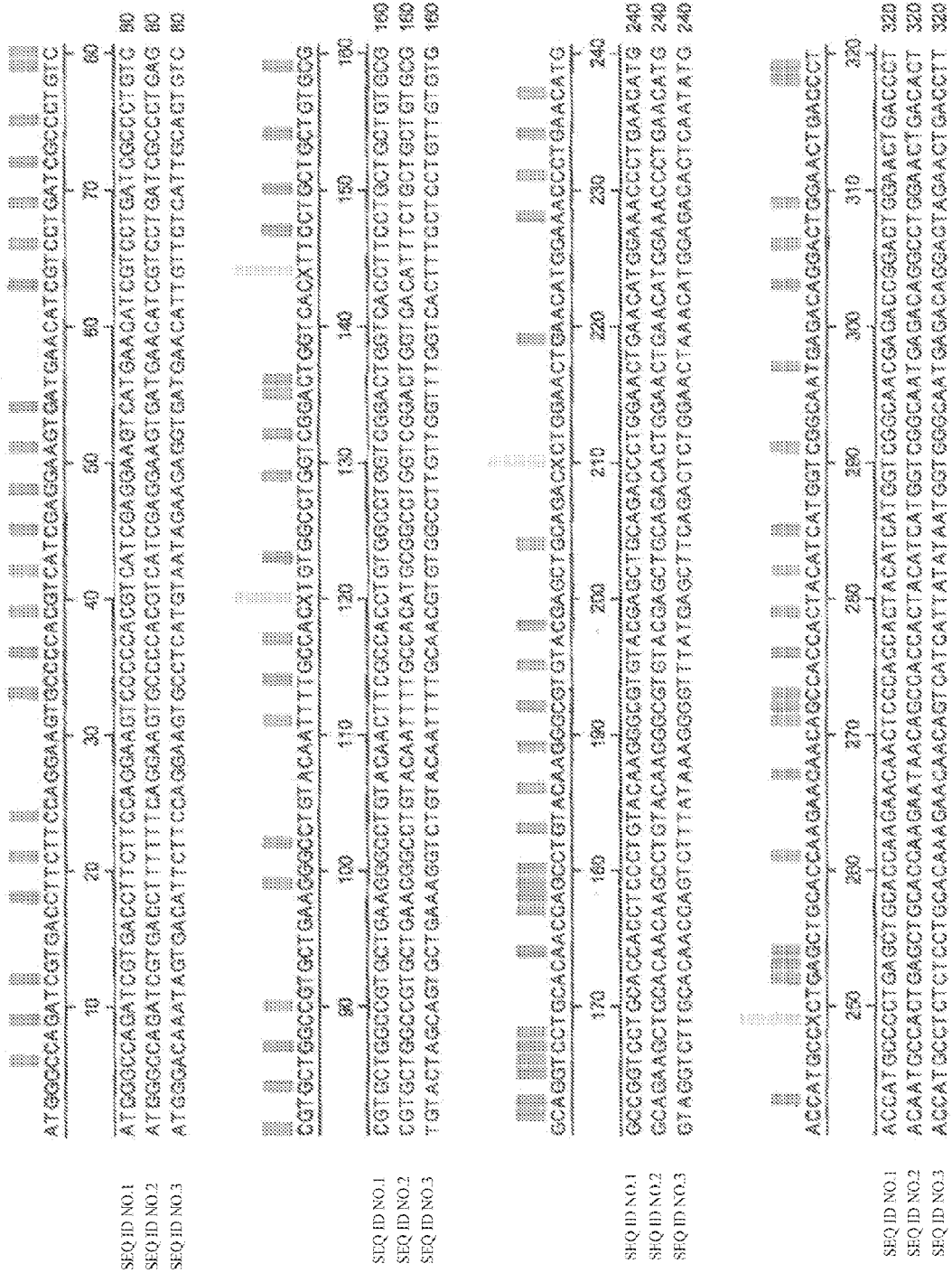
FIG. 8 displays a sequence alignment between LASV-GPC codon optimized for guinea pigs (LASV-GPC GP), LASV-GPC codon optimized for non-human primate (LASV-GPC NHP), and reference LASV GPC (control).
Figure 8:
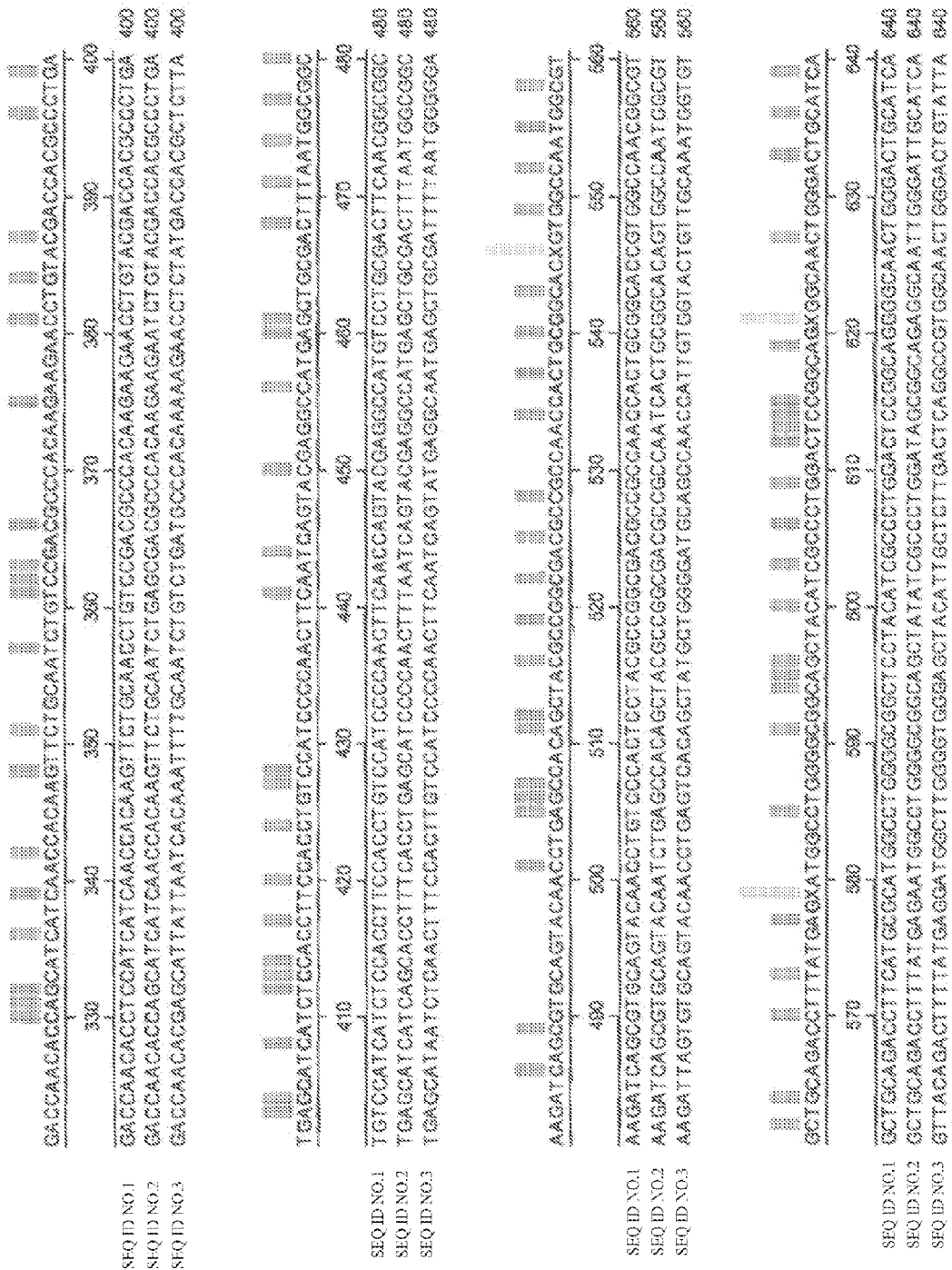
Figure 8:
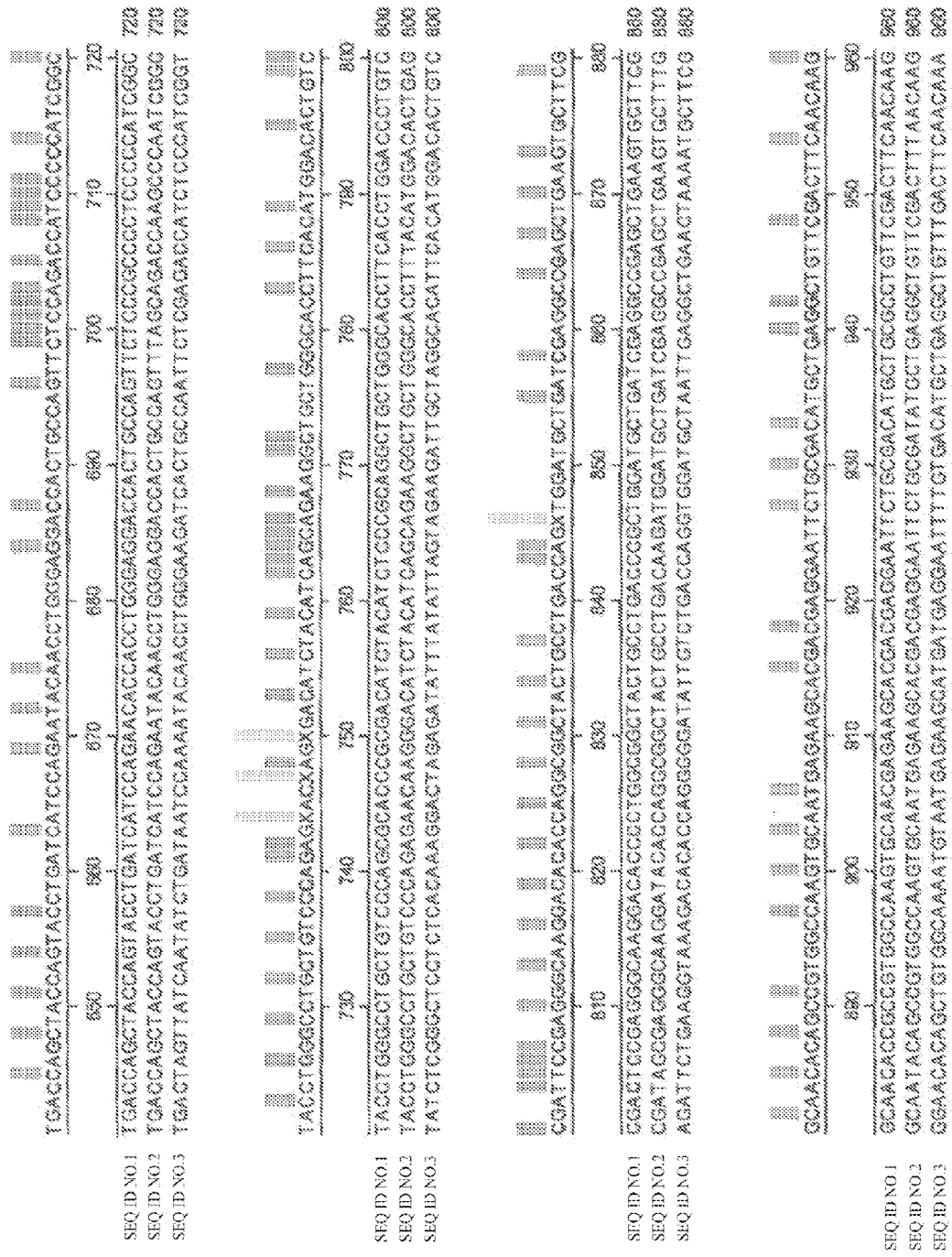

FIG. 7 displays CBCs and blood chemistries of vaccinated *cynomolgus* (NHPs), both vaccinated with the LASV-GPC (comprising SEQ ID NO:2) and mock DNA vaccine. The results displayed show CBCs and blood chemistries normal in the NHPs.

Experiments and Methods

Perform Dose Ranging Study of LASV DNA Vaccine (Months 1-8)

Three doses of LASV DNA vaccine in Strain 13 guinea pigs are to be assessed. In previous studies, three vaccinations of 50 µg of the LASV DNA vaccine given by MID EP at 3-week intervals provided complete protective immunity to Strain 13 guinea pigs. The vaccines protective efficacy in a shortened regime (two vaccinations given 3 weeks apart) of 50 µg, 5 µg and 1 µg doses given by MID EP (Table 1) will be compared.

TABLE 1

Dose ranging assessment of the LASV codon optimized DNA vaccine delivered by intradermal electroporation to Strain 13 guinea pigs.

| Group | DNA Vaccine | Dose | # guinea pigs | Vaccination Schedule | Challenge virus |
|---|---|---|---|---|---|
| 1 | LASV | 50 µg | 8 | 0, 4 weeks | LASV |
| 2 | LASV | 5 µg | 8 | 0, 4 weeks | LASV |
| 3 | LASV | 1 µg | 8 | 0, 4 weeks | LASV |
| 4 | Empty vector | 50 µg | 8 | 0, 4 weeks | LASV |
| | Total = | | 32 | | |

Determination of Cross Protection of JUNV and MACV DNA Vaccines and Measure Interference of Multi-Agent Vaccine Formulation The overall applicability of the DNA vaccine-dermal electroporation system as a multi-agent vaccine platform will be tested. Codon optimized DNA vaccines for JUNV and MACV (which share about 96% GPC amino acid homology) will be generated and a cross challenge study (Table 2) will be performed. Upon determination that the JUNV and MACV vaccines are cross protective, then future studies aimed at protection from both Old World and New World arenaviruses can use only one of the two vaccines in combination with the LASV vaccine. A group of guinea pigs in this study will be vaccinated with all three of the candidate DNA vaccines and challenged with LASV.

TABLE 2

Pilot study to assess: (1) cross protection of JUNV and MACV codon optimized DNA vaccines; and (2) multi-agent potential of the vaccine platform.

| Group | DNA Vaccine | Dose | # guinea pigs | Vaccination Schedule | Challenge virus |
|---|---|---|---|---|---|
| 1 | JUNV | 75 µg | 8 | 0, 4 weeks | JUNV |
| 2 | JUNV | 75 µg | 8 | 0, 4 weeks | MACV |
| 3 | MACV | 75 µg | 8 | 0, 4 weeks | MACV |
| 4 | MACV | 75 µg | 8 | 0, 4 weeks | JUNV |
| 5 | Empty Vector | 75 µg | 8 | 0, 4 weeks | JUNV |
| 6 | Empty Vector | 75 µg | 8 | 0, 4 weeks | MACV |
| 7 | LASV, JUNV, MACV | 25 µg each | 8 | 0, 4 weeks | LASV |
| 8 | Empty Vector | 75 µg | 8 | 0, 4 weeks | LASV |
| | Total = | | 64 | | |

Measure Immune Correlates, Dose Reduction and Cytokine Adjuvants in NHP Challenge Model Studies will be performed to measure immune responses of nonhuman primates (NHP) vaccinated with the LASV DNA vaccine (comprising SEQ ID NO:2) by EP, with and without cytokine adjuvants (see list in Table 3, below). After vaccination, the NHP will be challenged in a BSL-4 containment laboratory.

Two cytokine DNA plasmids will be tested in combination with the LASV DNA vaccine, IL-28, and IL-12.

NHPs vaccinated three times at 3-week intervals with 1 mg of LASV DNA vaccine (comprising SEQ ID NO:2) were shown in earlier studies showed protection from a challenge with LASV. Studies will be performed that compare 1 mg doses of the vaccine given three times at 4-week intervals to the same dose given two times 8-weeks apart. In addition, a half-strength dose of vaccine (0.5 mg) given alone or in combination with plasmids expressing the genes of IL-12 or IL-28 cytokines will be compared. These cytokines are intended to adjuvant the vaccine and provide improved cell mediated immune responses.

The cellular immune phenotypes induced by the LASV vaccine and the cytokine adjuvants will be assessed by the following analyses: antigen-specific IFNg ELISPOT, intracellular cytokine staining (including assaying for polyfunctional T cell profiles), proliferation via CFSE-dilution, and staining for markers of cytolytic CD8+ T cells including expression of Tbet, Peforin, Granzyme B and CD107a as described in Hersperger et al 2010a, Hersperger et al 2010b, Morrow et al 2010b and Migueles et al 2008. The combination of these immunoassays will allow specific interrogation of the CD8+ T cell response to the LASV DNA vaccine, with special emphasis on CTL (cytotoxic lymphocyte) phenotype and activity, as this function of CD8+ T cells is directly correlated with elimination of virally infected cells and constitutes a major mechanism by which the immune system controls and eliminates viral infection. Previous studies employing IL-12 and IL-28 have suggested that both of these adjuvants are able to drive the induction of vaccine specific CTLs that exhibited robust increases in Perforin release, Granzyme B loading and release, and expression of CD107a. That study was performed in an NHP model using HIV antigens in addition to adjuvant, and these increased responses were seen both in PBMCs as well as T cells harvested from Mesenteric Lymph Nodes, suggesting that these adjuvants exert influence in peripheral blood as well as secondary lymphoid organs. Moreover, both IL-12 and IL-28 were able to exert their influence on CTL phenotypes and function on a long-term basis, as analysis performed 3 months after the final immunization showed a continued presence of augmented antigen specific immune responses.

TABLE 3

Dosing in NHP with and without IL-12 or IL-28 adjuvants.

| Group | DNA Vaccine(s) | Dose | # NHP | Vaccination Schedule | Challenge virus |
|---|---|---|---|---|---|
| 1 | LASV | 1 mg | 4 | 0, 4, 8 weeks | LASV |
| 2 | LASV | 1 mg | 4 | 0, 8 weeks | LASV |
| 3 | LASV | 0.5 mg | 4 | 0, 8 weeks | LASV |
| 4 | LASV + IL-28 | 0.5 mg each | 4 | 0, 8 weeks | LASV |
| 5 | LASV + IL-12 | 0.5 mg each | 4 | 0, 8 weeks | LASV |

TABLE 3-continued

Dosing in NHP with and without IL-12 or IL-28 adjuvants.

| Group | DNA Vaccine(s) | Dose | # NHP | Vaccination Schedule | Challenge virus |
|---|---|---|---|---|---|
| 5 | Empty Vector | 1 mg | 4 | 0, 8 weeks | LASV |
| | Total = | | 24 | | |

Development of Potency Assay for LASV DNA Vaccine

To enable IND submission, a robust and reliable potency assay will be needed. A quantitative flow cytometry assay potency assay is to be used for the AV vaccines, for example the LASV DNA vaccine. Similar assays have already been developed and have been used for more than three years at USAMRIID in support of a Phase 1 clinical study of a DNA vaccine for hemorrhagic fever with renal syndrome caused by hantavirus infections (Badger et al. 2011) and to support IND submission of a DNA vaccine for Venezuelan equine encephalitis virus. In general, the method involves transfecting cells with test DNA and comparing the measured antigen expression to that generated with expression from known quantities of reference material DNA.

The assay is rapid (less than one day) highly reproducible and has already been adapted for performance under Good Laboratory Practice (GLP) guidelines. Consequently, regulatory documents and procedures are already in place. This should greatly facilitate adaptation of the assay for measuring the potency of the LASV DNA vaccine. Although this assay alone is sufficient to measure potency and stability of the DNA vaccine, because there are few correlates of protective immunity for LASV infection, we will also vaccinate small groups of guinea pigs at each stability time point for the first year to provide information correlating gene expression to antigenicity.

The guinea pig challenge model is an accepted model for AV assessing AV vaccine efficacy. The animals were vaccinated 3× at 3-4 week intervals with 50 ug of the GPC DNA LASV vaccine using the MID device. The animals were challenged by i.m. injection with 1000 pfu of LASV three weeks after the last vaccination. As shown in FIG. 2 greater than 90% of the vaccinated animals survived the challenge while 100% of the control (mock vaccinated) animals died by day 15 post challenge. FIG. 5 shows challenge data from the NHP study. Groups of 4 NHPs were vaccinated with 1 mg GPC DNA LASV vaccine or 1 mg of empty vector 3× at 3-week intervals and challenged by i.m. injection of 1000 pfu LASV 4 weeks after final vaccination. 4/4 vaccinated NHP survived and showed no signs of viremia while 4/4 control animal developed viremia and 2/4 succumbed to the challenge.

The invention claimed is:

1. A DNA vaccine comprising a nucleotide coding sequence that encodes one or more immunogenic proteins capable of generating a protective immune response against an arenavirus in a subject in need thereof, comprising:
a coding sequence encoding a glycoprotein precursor of an arenavirus, optimized for said subject, wherein the coding sequence is SEQ ID NO: 1 or 2.

2. The DNA vaccine of claim 1, wherein said coding sequence consists essentially of a coding sequence encoding a glycoprotein precursor domain of lassa virus (LASV-GPC).

3. The DNA vaccine of claim 1, further comprising an adjuvant selected from the group consisting of interleukin-12, interleukin-15, interleukin-28 and RANTES (regulated on activation, normal T-cell expressed and secreted).

4. A method of inducing a protective immune response against an arenavirus comprising:
administering a DNA vaccine of claim 1 or 2 to a subject in need thereof, and electroporating said subject.

5. The method of claim 4, wherein the electroporating step comprises:
delivering an electroporating pulse of energy to a site on said subject that administration step occurred.

6. The method of claim 5, wherein the administrating step and electroporating step both occur in an intradermal layer of said subject.

7. The DNA vaccine of claim 1 or 2, wherein said DNA vaccine consists essentially of one of said coding sequences.

8. The DNA vaccine of claim 1 or 2, wherein said DNA vaccine consists essentially of at least two of said coding sequences.

* * * * *

SEQUENCE LISTING

<160> NUMBER OF SEQ ID NOS: 6

<210> SEQ ID NO 1
<211> LENGTH: 1476
<212> TYPE: DNA
<213> ORGANISM: Artificial Sequence
<220> FEATURE:
<223> OTHER INFORMATION: LASV Josiah GP

<400> SEQUENCE: 1

```
atgggccaga tcgtgacctt cttccaggaa gtcccccacg tcatcgagga agtcatgaac      60
atcgtcctga tcgccctgtc cgtgctggcc gtgctgaagg gcctgtacaa cttcgccacc     120
```

```
tgtggcctgg tcggactggt caccttcctg ctgctgtgcg gccggtcctg caccacctcc      180
ctgtacaagg gcgtgtacga gctgcagacc ctggaactga acatggaaac cctgaacatg      240
accatgcccc tgagctgcac caagaacaac tcccaccact acatcatggt cggcaacgag      300
accggactgg aactgaccct gaccaacacc tccatcatca accacaagtt ctgcaacctg      360
tccgacgccc acaagaagaa cctgtacgac cacgccctga tgtccatcat ctccaccttc      420
cacctgtcca tccccaactt caaccagtac gaggccatgt cctgcgactt caacggcggc      480
aagatcagcg tgcagtacaa cctgtcccac tcctacgccg gcgacgccgc caaccactgc      540
ggcaccgtgg ccaacggcgt gctgcagacc ttcatgcgca tggcctgggg cggctcctac      600
atcgccctgg actccggcag gggcaactgg gactgcatca tgaccagcta ccagtacctg      660
atcatccaga acaccacctg ggaggaccac tgccagttct cccgcccctc ccccatcggc      720
tacctgggcc tgctgtccca gcgcacccgc gacatctaca tctcccgcag gctgctgggc      780
accttcacct ggaccctgtc cgactccgag ggcaaggaca cccctggcgg ctactgcctg      840
acccgctgga tgctgatcga ggccgagctg aagtgcttcg gcaacaccgc cgtggccaag      900
tgcaacgaga agcacgacga ggaattctgc gacatgctgc gcctgttcga cttcaacaag      960
caggccatcc agcgcctgaa ggccgaggcc agatgtctca tccagctgat caacaaggcc     1020
gtgaacgccc tgatcaacga tcagctcatc atgaagaacc cctgaggga catcatgggc      1080 atcccttact gcaactactc caagtactgg tatctgaacc acaccaccac cggccgcacc     1140
tccctgccca gtgctggct ggtgtccaac ggctcctacc tgaacgagac ccacttctcc      1200
gacgacatcg agcagcaggc cgacaacatg atcaccgaga tgctgcagaa agaatacatg      1260
gaacgccaag gcaagacacc actgggcctg gtggacctgt cgtgttctc cacctccttc      1320 tacctgatct ccatcttcct gcacctggtc aagatcccca cccaccgcca catcgtgggc      1380
aagtcctgcc ccaagcccca caggctgaac cacatgggca tctgcagctg cggactgtac     1440
aagcagcccg gcgtgcccgt gaagtggaag cgctga                              1476
```

<210> SEQ ID NO 2
<211> LENGTH: 1476
<212> TYPE: DNA
<213> ORGANISM: Artificial Sequence
<220> FEATURE:
<223> OTHER INFORMATION: LASV Josiah NHP

<400> SEQUENCE: 2

```
atgggccaga tcgtgacctt ttttcaggaa gtgccccacg tcatcgagga agtgatgaac       60
atcgtcctga tcgccctgag cgtgctggcc gtgctgaagg gcctgtacaa ttttgccaca      120
tgcggcctgg tcggactggt cacatttctg ctgctgtgcg gcagaagctg cacaacaagc      180
ctgtacaagg gcgtgtacga gctgcagaca ctggaactga acatggaaac cctgaacatg      240
acaatgccac tgagctgcac caagaataac agccaccact acatcatggt cggcaatgag      300
acaggcctgg aactgacact gaccaacacc agcatcatca accacaagtt ctgcaatctg      360
agcgacgccc acaagaagaa tctgtacgac cacgccctga tgagcatcat cagcaccttt      420
cacctgagca tccccaactt taatcagtac gaggccatga gctgcgactt taatggcggc      480
aagatcagcg tgcagtacaa tctgagccac agctacgccg gcgacgccgc caatcactgc      540
ggcacagtgg ccaatggcgt gctgcagacc tttatgagaa tggcctgggg cggcagctat      600
atcgccctgg atagcggcag aggcaattgg gattgcatca tgaccagcta ccagtacctg      660
```

| | |
|---|---|
| atcatccaga atacaacctg ggaggaccac tgccagttta gcagaccaag cccaatcggc | 720 |
| tacctgggcc tgctgtccca gagaacaagg gacatctaca tcagcagaag gctgctgggc | 780 |
| acctttacat ggacactgag cgatagcgag ggcaaggata caccaggcgg ctactgcctg | 840 |
| acaagatgga tgctgatcga ggccgagctg aagtgctttg caatacagc cgtggccaag | 900 |
| tgcaatgaga agcacgacga ggaattctgc gatatgctga ggctgttcga ctttaacaag | 960 |
| caggccatcc agagactgaa ggccgaggcc cagatgtcca tccagctgat caataaggcc | 1020 |
| gtgaacgccc tgatcaatga ccagctgatc atgaagaacc acctgagaga catcatgggc | 1080 |
| atcccatact gcaactacag caagtactgg tatctgaacc acacaacaac aggcagaaca | 1140 |
| agcctgccaa agtgctggct ggtgtccaat ggcagctacc tgaacgagac acactttagc | 1200 |
| gacgatatcg agcagcaggc cgacaatatg atcacagaga tgctgcagaa agaatacatg | 1260 |
| gaaaggcagg gcaagacacc actgggcctg gtggatctgt ttgtgttcag caccagcttc | 1320 |
| tacctgatca gcatctttct gcacctggtc aagatcccaa cacacagaca catcgtgggc | 1380 |
| aagagctgcc aaaagccaca cagactgaac acatgggca tctgcagctg cggcctgtat | 1440 |
| aagcagccag gcgtgccagt gaagtggaag agatga | 1476 |

<210> SEQ ID NO 3
<211> LENGTH: 1476
<212> TYPE: DNA
<213> ORGANISM: Artificial Sequence
<220> FEATURE:
<223> OTHER INFORMATION: LASV ref gp2

<400> SEQUENCE: 3

| | |
|---|---|
| atgggacaaa tagtgacatt cttccaggaa gtgcctcatg taatagaaga ggtgatgaac | 60 |
| attgttctca ttgcactgtc tgtactagca gtgctgaaag gtctgtacaa ttttgcaacg | 120 |
| tgtggccttg ttggtttggt cactttcctc ctgttgtgtg gtaggtcttg cacaaccagt | 180 |
| ctttataaag gggtttatga gcttcagact ctggaactaa acatggagac actcaatatg | 240 |
| accatgcctc tctcctgcac aaagaacaac agtcatcatt atataatggt gggcaatgag | 300 |
| acaggactag aactgagctt gaccaacacg agcattatta tcacaaaatt ttgcaatctg | 360 |
| tctgatgccc acaaaaagaa cctctatgac cacgctctta tgagcataat ctcaactttc | 420 |
| cacttgtcca tccccaactt caatcagtat gaggcaatga gctgcgattt taatggggga | 480 |
| aagattagtg tgcagtacaa cctgagtcac agctatgctg gggatgcagc caaccattgt | 540 |
| ggtactgttg caaatggtgt gttacagact tttatgagga tggcttgggg tgggagctac | 600 |
| attgctcttg actcaggccg tggcaactgg gactgtatta tgactagtta tcaatatctg | 660 |
| ataatccaaa atacaacctg ggaagatcac tgccaattct cgagaccatc tcccatcggt | 720 |
| tatctcgggc tcctctcaca aaggactaga gatatttata ttagtagaag attgctaggc | 780 |
| acattcacat ggacactgtc agattctgaa ggtaaagaca caccagggggg atattgtctg | 840 |
| accaggtgga tgctaattga ggctgaacta aaatgcttcg ggaacacagc tgtggcaaaa | 900 |
| tgtaatgaga agcatgatga ggaattttgt gacatgctga ggctgtttga cttcaacaaa | 960 |
| caagccattc aaaggttgaa agctgaagca caaatgagca ttcagttgat caacaaagca | 1020 |
| gtaaatgctt tgataaatga ccaacttata atgaagaacc atctacggga catcatggga | 1080 |
| attccatact gtaattacag caagtattgg tacctcaacc acacaactac tgggagaaca | 1140 |
| tcactgccca atgttggct tgtatcaaat ggttcatact tgaacgagac ccactttct | 1200 |
| gatgatattg aacaacaagc tgacaatatg atcactgaga tgttacagaa ggagtatatg | 1260 |

-continued

```
gagaggcagg ggaagacacc attgggtcta gttgacctct tgtgttcag tacaagtttc    1320 tatcttatta gcatcttcct tcacctagtc aaaataccaa ctcataggca tattgtaggc    1380
aagtcgtgtc ccaaacctca cagattgaat catatgggca tttgttcctg tggactctac    1440
aaacagcctg gtgtgcctgt gaaatggaag agatga                              1476
```

<210> SEQ ID NO 4
<211> LENGTH: 491
<212> TYPE: PRT
<213> ORGANISM: Artificial Sequence
<220> FEATURE:
<223> OTHER INFORMATION: LASV Josiah GP (amino acid)

<400> SEQUENCE: 4

```
Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
            20                  25                  30

Lys Gly Leu Tyr Asn Phe Ala Thr Cys Gly Leu Val Gly Leu Val Thr
        35                  40                  45

Phe Leu Leu Leu Cys Gly Arg Ser Cys Thr Thr Ser Leu Tyr Lys Gly
    50                  55                  60

Val Tyr Glu Leu Gln Thr Leu Glu Leu Asn Met Glu Thr Leu Asn Met
65                  70                  75                  80

Thr Met Pro Leu Ser Cys Thr Lys Asn Asn Ser His His Tyr Ile Met
                85                  90                  95

Val Gly Asn Glu Thr Gly Leu Glu Leu Thr Leu Thr Asn Thr Ser Ile
            100                 105                 110

Ile Asn His Lys Phe Cys Asn Leu Ser Asp Ala His Lys Lys Asn Leu
        115                 120                 125

Tyr Asp His Ala Leu Met Ser Ile Ile Ser Thr Phe His Leu Ser Ile
    130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
                165                 170                 175

Ala Asn His Cys Gly Thr Val Ala Asn Gly Val Leu Gln Thr Phe Met
            180                 185                 190

Arg Met Ala Trp Gly Gly Ser Tyr Ile Ala Leu Asp Ser Gly Arg Gly
        195                 200                 205

Asn Trp Asp Cys Ile Met Thr Ser Tyr Gln Tyr Leu Ile Ile Gln Asn
    210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
                245                 250                 255

Arg Leu Leu Gly Thr Phe Thr Trp Thr Leu Ser Asp Ser Glu Gly Lys
            260                 265                 270

Asp Thr Pro Gly Gly Tyr Cys Leu Thr Arg Trp Met Leu Ile Glu Ala
        275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320
```

```
Gln Ala Ile Gln Arg Leu Lys Ala Glu Ala Gln Met Ser Ile Gln Leu
                325                 330                 335

Ile Asn Lys Ala Val Asn Ala Leu Ile Asn Asp Gln Leu Ile Met Lys
            340                 345                 350

Asn His Leu Arg Asp Ile Met Gly Ile Pro Tyr Cys Asn Tyr Ser Lys
        355                 360                 365

Tyr Trp Tyr Leu Asn His Thr Thr Thr Gly Arg Thr Ser Leu Pro Lys
    370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
                405                 410                 415

Lys Glu Tyr Met Glu Arg Gln Gly Lys Thr Pro Leu Gly Leu Val Asp
            420                 425                 430

Leu Phe Val Phe Ser Thr Ser Phe Tyr Leu Ile Ser Ile Phe Leu His
        435                 440                 445

Leu Val Lys Ile Pro Thr His Arg His Ile Val Gly Lys Ser Cys Pro
    450                 455                 460

Lys Pro His Arg Leu Asn His Met Gly Ile Cys Ser Trp Gly Leu Tyr
465                 470                 475                 480

Lys Gln Pro Gly Val Pro Val Lys Trp Lys Arg
                485                 490

<210> SEQ ID NO 5
<211> LENGTH: 491
<212> TYPE: PRT
<213> ORGANISM: Artificial Sequence
<220> FEATURE:
<223> OTHER INFORMATION: LASV Josiah NHP (amino acid)

<400> SEQUENCE: 5

Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
                20                  25                  30

Lys Gly Leu Tyr Asn Phe Ala Thr Cys Gly Leu Val Gly Leu Val Thr
            35                  40                  45

Phe Leu Leu Leu Cys Gly Arg Ser Cys Thr Thr Ser Leu Tyr Lys Gly
        50                  55                  60

Val Tyr Glu Leu Gln Thr Leu Glu Leu Asn Met Glu Thr Leu Asn Met
65                  70                  75                  80

Thr Met Pro Leu Ser Cys Thr Lys Asn Asn Ser His His Tyr Ile Met
                85                  90                  95

Val Gly Asn Glu Thr Gly Leu Glu Leu Thr Leu Thr Asn Thr Ser Ile
                100                 105                 110

Ile Asn His Lys Phe Cys Asn Leu Ser Asp Ala His Lys Lys Asn Leu
            115                 120                 125

Tyr Asp His Ala Leu Met Ser Ile Ile Ser Thr Phe His Leu Ser Ile
        130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
                165                 170                 175

Ala Asn His Cys Gly Thr Val Ala Asn Gly Val Leu Gln Thr Phe Met
                180                 185                 190
```

Arg Met Ala Trp Gly Gly Ser Tyr Ile Ala Leu Asp Ser Gly Arg Gly
            195                 200                 205

Asn Trp Asp Cys Ile Met Thr Ser Tyr Gln Tyr Leu Ile Ile Gln Asn
        210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
                245                 250                 255

Arg Leu Leu Gly Thr Phe Thr Trp Thr Leu Ser Asp Ser Glu Gly Lys
            260                 265                 270

Asp Thr Pro Gly Gly Tyr Cys Leu Thr Arg Trp Met Leu Ile Glu Ala
        275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320

Gln Ala Ile Gln Arg Leu Lys Ala Glu Ala Gln Met Ser Ile Gln Leu
                325                 330                 335

Ile Asn Lys Ala Val Asn Ala Leu Ile Asn Asp Gln Leu Ile Met Lys
            340                 345                 350

Asn His Leu Arg Asp Ile Met Gly Ile Pro Tyr Cys Asn Tyr Ser Lys
        355                 360                 365

Tyr Trp Tyr Leu Asn His Thr Thr Gly Arg Thr Ser Leu Pro Lys
    370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
                405                 410                 415

Lys Glu Tyr Met Glu Arg Gln Gly Lys Thr Pro Leu Gly Leu Val Asp
            420                 425                 430

Leu Phe Val Phe Ser Thr Ser Phe Tyr Leu Ile Ser Ile Phe Leu His
        435                 440                 445

Leu Val Lys Ile Pro Thr His Arg His Ile Val Gly Lys Ser Cys Pro
    450                 455                 460

Lys Pro His Arg Leu Asn His Met Gly Ile Cys Ser Cys Gly Leu Tyr
465                 470                 475                 480

Lys Gln Pro Gly Val Pro Val Lys Trp Lys Arg
                485                 490

<210> SEQ ID NO 6
<211> LENGTH: 491
<212> TYPE: PRT
<213> ORGANISM: Artificial Sequence
<220> FEATURE:
<223> OTHER INFORMATION: LASV reference (amino acid)

<400> SEQUENCE: 6

Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
            20                  25                  30

Lys Gly Leu Tyr Asn Phe Ala Thr Cys Gly Leu Val Gly Leu Val Thr
        35                  40                  45

Phe Leu Leu Leu Cys Gly Arg Ser Cys Thr Thr Ser Leu Tyr Lys Gly

```
            50                  55                  60
Val Tyr Glu Leu Gln Thr Leu Glu Leu Asn Met Glu Thr Leu Asn Met
 65                  70                  75                  80

Thr Met Pro Leu Ser Cys Thr Lys Asn Asn Ser His His Tyr Ile Met
                 85                  90                  95

Val Gly Asn Glu Thr Gly Leu Glu Leu Ser Leu Thr Asn Thr Ser Ile
                100                 105                 110

Ile Asn His Lys Phe Cys Asn Leu Ser Asp Ala His Lys Lys Asn Leu
                115                 120                 125

Tyr Asp His Ala Leu Met Ser Ile Ile Ser Thr Phe His Leu Ser Ile
            130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
                165                 170                 175

Ala Asn His Cys Gly Thr Val Ala Asn Gly Val Leu Gln Thr Phe Met
                180                 185                 190

Arg Met Ala Trp Gly Gly Ser Tyr Ile Ala Leu Asp Ser Gly Arg Gly
            195                 200                 205

Asn Trp Asp Cys Ile Met Thr Ser Tyr Gln Tyr Leu Ile Ile Gln Asn
    210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
                245                 250                 255

Arg Leu Leu Gly Thr Phe Thr Trp Thr Leu Ser Asp Ser Glu Gly Lys
                260                 265                 270

Asp Thr Pro Gly Gly Tyr Cys Leu Thr Arg Trp Met Leu Ile Glu Ala
            275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320

Gln Ala Ile Gln Arg Leu Lys Ala Glu Ala Gln Met Ser Ile Gln Leu
                325                 330                 335

Ile Asn Lys Ala Val Asn Ala Leu Ile Asn Asp Gln Leu Ile Met Lys
            340                 345                 350

Asn His Leu Arg Asp Ile Met Gly Ile Pro Tyr Cys Asn Tyr Ser Lys
    355                 360                 365

Tyr Trp Tyr Leu Asn His Thr Thr Thr Gly Arg Thr Ser Leu Pro Lys
370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
                405                 410                 415

Lys Glu Tyr Met Glu Arg Gln Gly Lys Thr Pro Leu Gly Leu Val Asp
            420                 425                 430

Val Phe Val Phe Ser Thr Ser Phe Tyr Leu Ile Ser Ile Phe Leu His
            435                 440                 445

Leu Val Lys Ile Pro Thr His Arg His Ile Val Gly Lys Ser Cys Pro
450                 455                 460

Lys Pro His Arg Leu Asn His Met Gly Ile Cys Ser Cys Gly Leu Tyr
465                 470                 475                 480
```

```
Lys Gln Pro Gly Val Pro Val Lys Trp Lys Arg
            485                 490
```